US007888075B2

(12) United States Patent
McCarthy et al.

(10) Patent No.: US 7,888,075 B2
(45) Date of Patent: Feb. 15, 2011

(54) **DETECTION OF METHICILLIN-RESISTANT AND METHICILLIN-SENSITIVE *STAPHYLOCOCCUS AUREUS* IN BIOLOGICAL SAMPLES**

(75) Inventors: Larry McCarthy, Great Falls, VA (US); Lilly Kong, Covina, CA (US); Michelle Tabb, Santa Ana, CA (US); Ming-Chou Lee, Mission Viejo, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 139 days.

(21) Appl. No.: 12/177,075

(22) Filed: Jul. 21, 2008

(65) Prior Publication Data

US 2009/0035780 A1 Feb. 5, 2009

Related U.S. Application Data

(60) Provisional application No. 60/962,846, filed on Jul. 31, 2007.

(51) Int. Cl.
*C12Q 1/68* (2006.01)
*C12P 19/34* (2006.01)
(52) U.S. Cl. .......................... 435/91.2; 435/6; 435/91.1
(58) Field of Classification Search ........................ None
See application file for complete search history.

(56) References Cited

U.S. PATENT DOCUMENTS

| | | | |
|---|---|---|---|
| 5,135,717 | A | 8/1992 | Renzoni et al. |
| 5,437,978 | A | 8/1995 | Ubukata et al. |
| 5,652,099 | A | 7/1997 | Conrad |
| 5,702,895 | A | 12/1997 | Matsunaga et al. |
| 5,994,066 | A | 11/1999 | Bergeron et al. |
| 6,001,564 | A | 12/1999 | Bergeron et al. |
| 6,156,507 | A | 12/2000 | Hiramatsu et al. |
| 6,268,132 | B1 | 7/2001 | Conrad |
| 6,503,709 | B1 | 1/2003 | Bekkaoui et al. |
| 6,913,881 | B1 | 7/2005 | Aizenstein et al. |
| 6,960,436 | B2 | 11/2005 | Cottrell |
| 2002/0098492 | A1 | 7/2002 | Taya et al. |
| 2004/0063103 | A1 | 4/2004 | Uhl et al. |
| 2004/0086944 | A1 | 5/2004 | Grigg et al. |
| 2004/0219539 | A1 | 11/2004 | Millar et al. |
| 2004/0241824 | A1 | 12/2004 | Schrenzel et al. |
| 2005/0019893 | A1 | 1/2005 | Huletsky et al. |
| 2005/0042606 | A9 | 2/2005 | Bergeron et al. |
| 2005/0059064 | A1 | 3/2005 | Obst et al. |
| 2007/0020633 | A1 | 1/2007 | Millar et al. |
| 2007/0042365 | A1 | 2/2007 | Millar et al. |
| 2007/0082340 | A1 | 4/2007 | Huletsky et al. |
| 2009/0081663 | A1* | 3/2009 | Paitan ........................... 435/6 |

FOREIGN PATENT DOCUMENTS

| | | |
|---|---|---|
| EP | 0527628 | 7/1996 |
| EP | 1160333 | 1/2004 |
| EP | 1529847 | 4/2006 |
| EP | 1512756 | 3/2008 |
| WO | WO 2004/029299 | 4/2004 |
| WO | WO 2005/008222 | 1/2005 |
| WO | WO 2005/017202 | 2/2005 |
| WO | WO 2006/058393 | 6/2006 |

OTHER PUBLICATIONS

Presence of a Novel DNA Methylation Enzyme in Methicillin-Resistant *Staphylococcus aureus* Isolates Associated with Pig Farming Leads to Uninterpretable Results in Standard Pulsed-Field Gel Electrophoresis Analysis, Journal of Clinical Microbiology, May 2006, vol. 44, No. 5, pp. 1875-1876.*
Clark, S.J. et al., High sensitivity mapping of methylated cytosines, Nucl. Acids Res. 22: 2990-7 (1994).
Frommer, M. et al., A genomic sequencing protocol that yields a positive display of 5-methylcytosine residues in individual DNA strands, PNAS 89:1827-1831 (1992).
Hafner, G.J. et al., Isothermal Amplification and Multimerization of DNA by *Bst* DNA Polymerase, Biotechniques Apr:30(4):852-860 (2001).
Hanssen, A.-M. & Sollid, J.U.E., Multiple Staphylococcal Cassette Chromosomes and Allelic Variants of Cassette Chromosome Recombinases in *Staphylococcus aureus* and Coagulase-Negative Staphylococci from Norway, Antimicrob. Agents & Chemother. 51:1671 (2007).
Heid, C.A. et al., Real time quantitative PCR, Genome Res. 6:986-994 (1996).
Jameson, D.M. and Eccleston, J.F., Fluorescent Nucleotide Analogs: Synthesis and Applications, Meth. Enzymol. 278:363-390 (1997).
Maniatis, T. et al., DNA Transfection by Electroporation, Molecular Cloning, A Laboratory Manual, 2d, Cold Spring Harbor Laboratory Press, p. 16.54-16.55 (1989).
Mansfield, E.S. et al., Nucleic acid detection using non-radioactive labeling methods, Mol. Cell. Probes 9:145-156 (1995).
McClelland and Nelson, The effect of site specific methylation on restriction endonuclease digestion. Nucleic Acid Research, vol. 13 Supplement, p. r201-r207.
Saiki, Randall K., "Amplification of Genomic DNA" in PCR Protocols, Innis et al., Eds., Academic Press, San Diego, CA, pp. 13-20 (1990).
Tyagi, S. et al., Multicolor molecular beacons for allele discrimination, Nature Biotechnology 16:49-53 (1998).
Wharam, S.D. et al., Specific detection of DNA and RNA targets using a novel isothermal nucleic acid amplification assay based on the formation of a three-way junction structure, Nucleic Acids Res. Jun. 1;29(11):E54-E54 (1-8), (2001).

(Continued)

*Primary Examiner*—Young J Kim
(74) *Attorney, Agent, or Firm*—Foley & Lardner LLP

(57) ABSTRACT

Disclosed are methods of identifying a methicillin-resistant *Staphylococcus aureus* (MRSA) or methicillin-sensitive *Staphylococcus aureus* (MSSA) in a sample. The present invention provides a diagnostic method comprising modification of sequences of *S. aureus* by converting non-methylated cytosine residues ultimately into thymidine residues in the target nucleic acid. The invention further provides for the detection of modified sequences derived from the spa gene, the mecA gene, and the integrated SCCmec cassette of *S. aureus*.

29 Claims, 11 Drawing Sheets

OTHER PUBLICATIONS

Whitcombe, D. et al., Detection of PCR products using self-probing amplicons and fluorescence, Nature Biotech. 17:804-807 (1999).

Zhu, Z. et al., Directly labeled DNA probes using fluorescent nucleotides with different length linkers, Nucl. Acids Res. 22(16):3418-3422 (1994).

International Search report for PCT Patent Application No. PCT/US2008/070618.

Supplementary European Search Report for EPO Patent Application No. 08796356.7.

International Preliminary Report on Patentability dated Feb. 2, 2010 in application PCT/US2008/070618.

International Search Report dated Nov. 10, 2008 in application PCT/US2008/070816.

\* cited by examiner

SEQUENCE LISTING

<160> NUMBER OF SEQ ID NOS: 42

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aggcggttgt aagatgtttt tgtgtaggtt gtccgcct                            38

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aggcggaatg ttattttgtt raatgatagt gtccgcct                            38

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tatttgaaat gaaagattgt ggaggtta                                       28

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tatgatattg taaggtataa tttaatattt tatatatgta                          40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tattattaat tttttaattt aattgtagtt ttataattaa                          40

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gtatgatatt gtaaggtata atttaatatt ttatatatgt                          40

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatattgtat gatattgtaa ggtataattt aatatttta                           39

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ataaaattat ggttgaaata attgtattat ttatga                              36

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaagaagttg atttatatat tatgtattaa ataatggaa                           39

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agcgccaaca aatattacac caccaaatat aaggcgct                            38

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cttaaatcat ctttaaaact ttaaataaaa cca                                 33

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```
agcgccatta ttttctaata cactataaat taaaaaaatc tggcgct                    47

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tctttatata ttttatttac aacttattac ataccatca                             39

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agcgccattt aatccaccaa taacaaatac ggcgct                                36

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agccggctac attataaaac atccttatac aaaccggct                             39

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttacttaaaa taaaaaacta caaaaactaa ctatatcaaa                            40

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctctataaac atcatataat attacaaaat ataatcca                              38

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
taaaaaccac tactaaaaaa aatataaaaa tcca                                  34

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aactctactt tatattataa aattacaact aaaataacca                              40

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acaactaaaa taaccacatc atttataata tacttct                                 37

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acttactaca aacatctaat acaaaaaaaa atcaa                                   35

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaaaaaatca atttacacac catatattaa ataataa                                 37

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctcatatttt ttaattttat ttataataca cttct                                   35

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttttctcata ttttttaatt ttatttataa tacacttct                               39

```
<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agcggcaaat attaaatata cctaacttaa acactaatcg ccgct            45

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atctaataac ataacaccta ctacaaatac tacacaa                     37

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agcgccgtgt ttatagattg aaaggatttg tattggcgct                  40

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gttttttaat aagtgaggtg tgttaatatt gtta                        34

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aggccaccag atataagtaa tgtacctaaa gtggcct                     37

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acttgataaa aagcattttg ttgagct                                27
```

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agccgctata gattgaaagg atctgtactg gcggct                           36

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtgaggtgcg ttaatattgc catta                                       25

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
aaaacaaaac aactttatwt tcatcattaa ca                               32

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
aacaacctac acaaaaacat cttacaaca                                   29

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ttaggtgtag gtattgtatt tgtaattta ggtata                            36

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
tttaggttat ggataaggtg aaatattgat ta                               32

<210> SEQ ID NO 37

```
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
gaattgaatt aatgtatgat ttaagggtaa agtga                              35

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
gtgattttgt atttgttatt ggtggatta                                     29

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
tttggattat ttttaaggtt ttggataaaa tta                                33

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
actgattcaa attacaaaca aaataaaata ctaa                               34

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
attcgtaaac taggtgtagg tattgca                                       27

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
aggttacgga caaggtgaaa tactga                                        26
```

DETECTION OF METHICILLIN-RESISTANT AND METHICILLIN-SENSITIVE *STAPHYLOCOCCUS AUREUS* IN BIOLOGICAL SAMPLES

CROSS-REFERENCE TO RELATED APPLICATIONS

This application claims the benefit of U.S. Provisional Application No. 60/962,846, filed Jul. 31, 2007, hereby incorporated by reference in its entirety.

FIELD OF THE INVENTION

The present invention relates generally to methods of pathogen detection. In particular, the present invention relates to methods of detecting methicillin-sensitive (MSSA) and/or methicillin-resistant *Staphylococcus aureus* (MRSA) in a biological sample.

BACKGROUND OF THE INVENTION

The following description is provided to assist the understanding of the reader. None of the information provided or references cited is admitted to be prior art to the present invention.

*Staphylococcus aureus* (*S. aureus*) is a cause of a variety of conditions in humans, including skin infections (e.g. folliculitis, styes, cellulitis, impetigo, and furuneulosis), pneumonia, mastitis, phlebitis, meningitis, scalded skin syndrome, osteomyelitis, urinary tract infections, and food poisoning. *S. aureus* is also a major cause of hospital-acquired (HA or nosocomial) infection of surgical wounds. Therefore, it is desirable to have a diagnostic assay to detect *S. aureus*. Additionally, methicillin-resistant *S. aureus* (MRSA) has emerged and become exceedingly prevalent as a nosocomial pathogen. Therefore, it is also desirable to have a diagnostic assay that distinguishes methicillin-sensitive strains of *S. aureus* (MSSA) from methicillin-resistant strains.

MRSA is one of the two "most out of control" antibiotic resistant pathogens; vancomycin-resistant *enterococcus* is the other (Society for Healthcare and Epidemiology, SHEA guidelines 2003). Over 50% of nosocomial infections in intensive care units are due to MRSA (National Nosocomial Infections Surveillance System, NNIS report, January 1992-June 2004). Accordingly, MRSA represents a significant threat to public health.

Hospital acquired (HA) MRSA is typically controlled by monitoring patients and personnel for infection. Contact precautions and/or patient isolation may be appropriate when an infection develops or to prevent infections to individuals particularly at risk. The prevalence of Community acquired (CA) MRSA is also increasing. CA-MRSA is defined as MRSA acquired in persons with no known risk factors for MRSA infection (e.g. recent hospitalization, contact with infected patient). In clinical activities, the quick and reliable identification of MRSA has become important for the diagnosis and treatment of infected patients as well as for implementation and management of hospital infection control procedures.

Methicillin resistance is caused by the acquisition of an exogenous gene mecA that encodes penicillin-binding protein (PBP2a or PBP2'). mecA is carried on a mobile genetic element called Staphylococcal cassette chromosome mec (SCCmec) which also contains the ccr gene complex encoding the recombinases necessary for the element's mobility. The SCCmec cassette is a large element that can move in and out of the *S. aureus* genome. SCCmec integrates at a specific site (attBscc) near the chromosomal origin of replication of *S. aureus* within the 3' end of the orfx gene, which has no known function. There are a variety of different types of SCCmec defined by variability in length (approximately 20-60 kb), gene content and other factors such as ccr gene complex type.

The mecA gene is also present in coagulase-negative *Staphylococcus* (CNS) strains that are less pathogenic than *S. aureus*. These strains include *S. epidermidis, S. haemolyticus, S. saprophyticus, S. capitis, S. warneri, S. sciuri* and *S. caprae*. Some of these other strains of *Staphylococcus* inhabit the same environments as *S. aureus* such as the anterior nares and the skin. It follows that clinical samples such as nasal swabs or wound swabs could potentially contain a mixture of more than one Staphylococcal species. Therefore, detection of mecA alone is not sufficient to identify MRSA directly from clinical sample. Because identification of MRSA is of greater clinical significance than the other *Staphylococcus* species due to its increased pathogenicity and toxicity, it is desirable that a diagnostic assay distinguish MRSA from the other staphylococcal strains containing the mecA gene.

SUMMARY OF THE INVENTION

Accordingly, it is an object of the present invention to provide methods for detecting MRSA and/or MSSA in a biological sample. In particular, the present methods relate to the positive identification of MRSA and/or MSSA using detection of three gene markers. The present methods also relate to converting the nucleic acids in a sample so that unmethylated cytosine residues are replaced by thymidine residues and then to detecting sequence-modified MRSA and/or MSSA gene markers in the converted sample.

In some aspects, the present invention provides methods of detecting sequence-modified nucleic acids from *Staphylococcus aureus* in a biological sample, comprising converting the unmethylated cytosines present in the nucleic acids contained in the biological sample to uracils to produce sequence modified nucleic acids, and then bringing the biological sample containing the sequence modified nucleic acids in contact with one or more primer pairs that may be used to distinguish MRSA from MSSA and other Staphylococcal strains. In one embodiment, the one or more primer pairs may be selected from: (1) a first primer pair which is complementary to a segment of a marker gene specific for *Staphylococcus aureus* containing sequence modified nucleic acids; (2) a second primer pair which is complementary to a segment of the mecA gene containing sequence modified nucleic acids; and (3) a third primer pair, one primer of which is complementary to a segment of SCCmec containing sequence modified nucleic acids and the other primer of which is complementary to a segment of the orfx gene containing sequence modified nucleic acids under conditions wherein the primers specifically hybridize and an amplification product of the sequence-modified nucleic acids is produced. Two or more of the primer pairs may be combined in a single reaction vessel for multiplex detection of multiple sequence-modified MRSA markers. The methods may further comprise detecting an amplification product produced by one or more of the primer pairs, thereby detecting MRSA and/or MSSA, if present, in the sample of converted nucleic acids.

In another aspect, the present invention provides methods for determining if a biological sample from an individual contains methicillin resistant *Staphylococcus aureus* (MRSA) or methicillin sensitive *Staphylococcus aureus* (MSSA), comprising: (a) converting the non-methylated cytosines present in the nucleic acids contained in the biological sample, to uracils to produce sequence-modified nucleic acids; (b) bringing the biological sample containing the sequence modified nucleic acids in contact with: a first primer pair which is complementary to a segment of a marker gene specific for *Staphylococcus aureus* of the sequence modified nucleic acids; a second primer pair which is complementary to a segment of the mecA gene of the sequence modified nucleic acids; and a third primer pair, one primer of which is complementary to a segment of SCCmec of the sequence modified nucleic acids and the other primer of which is complementary to a segment of the orfx gene of the sequence modified nucleic acids under conditions wherein the primers specifically hybridize and amplification products of the sequence-modified nucleic acids are produced; and (c) identifying the modified nucleic acids from *Staphylococcus aureus* by detecting the amplification product produced by one or more of the primer pairs. In the methods, amplification of all three sequence-modified nucleic acids indicates MRSA in the sample; and amplification of the *S. aureus* specific marker gene alone, or integrated SCCmec and the *S. aureus* specific marker gene, but not mecA, indicates MSSA in the sample.

In some embodiments, the marker gene specific for *Staphylococcus aureus* may be selected from the group consisting of: spa, agr, ssp protease, sir, sodM, cap, coa, alpha hemolysin, gamma hemolysin, femA, Tuf sortase, fibrinogen binding protein, clfB, srC, sdrD, sdrE, sdrF, sdrG, sdrH, NAD synthetase, sar, sbi, rpoB, gyrase A, and orfX. In suitable embodiments, the marker gene specific for *S. aureus* is spa.

In certain embodiments of the methods described herein, the step of converting the non-methylated cytosines present in the nucleic acids contained in the biological sample to uracils is accomplished by contacting the nucleic acids with an agent (e.g. sodium bisulfite) capable of converting non-methylated cytosines to uracil.

In another aspect, the present invention provides methods of identifying methicillin resistant *Staphylococcus aureus* (MRSA) or methicillin sensitive *Staphylococcus aureus* (MSSA), if present, in a biological sample, comprising (a) bringing the biological sample in contact with: a first primer pair which is complementary to a marker gene specific for *Staphylococcus aureus*; a second primer pair which is complementary to the mecA gene; and a third primer pair, one primer of which is complementary to SCCmec and the other primer of which is complementary to the orfx gene; under conditions wherein the primers specifically hybridize and amplify the segments of the marker gene, mecA gene, SCCmec and orfx gene; and (b) identifying the MRSA by detecting an amplification product produced by all of the three primer pairs, wherein amplification of all three sequence-modified nucleic acids indicates MRSA in the sample; and amplification of the *S. aureus* specific marker gene alone, or integrated SCCmec and the *S. aureus* specific marker gene, but not mecA, indicates MSSA in the sample.

In some embodiments, any of the primers or probes may be degenerate, i.e. a mixture of primers or probes is provided that have a variable sequence at one or more nucleotide residues. The primers may be degenerate at 1 nucleotide position, 1-2 nucleotide positions, 1-3 nucleotide positions, and at 2, 3, 4, 5, 6, 7, 8, 9, 10 or more nucleotide positions.

The biological sample may be brought into contact with one or more of the primer pairs separately or simultaneously. Where the contact occurs simultaneously (i.e. multiplexing), one or more of the first primer pair, the second primer pair, and the third primer pair are brought into contact with the biological sample and with each other to amplify the target sequences. Optionally, a internal positive control nucleic acid and a fourth primer pair complementary to the internal positive control nucleic acid may be added to the amplification mixture.

In some aspects, the present methods use real time PCR to detect the amplification products. In certain embodiments, the detecting may be accomplished using a labeled oligonucleotide probe for each amplification product. A quencher may further be associated with the detectable label which prevents detection of the label prior to amplification of the probe's target. TaqMan® probes are examples of such probes. In some embodiments, the probe and one of the primers of the primer pair may comprise part of the same molecule (e.g. a Scorpion™ primer/probe). A Scorpion™ contains a fluorophore associated with a quencher to reduce background fluorescence. Following PCR extension, the synthesized target region is attached to the same strand as the probe. Upon denaturation, product, the probe portion of the Scorpion™ specifically hybridizes to a part of the newly produced PCR product, physically separating the fluorophore from the quencher, thereby producing a detectable signal.

In certain embodiments, at least one primer of each primer pair in the amplification reaction is labeled with a detectable moiety. Thus, following amplification, the various target segments can be identified by using different detectable moieties such as size and/or color. The detectable moiety may be a fluorescent dye. In some embodiments, different pairs of primers in a multiplex PCR may be labeled with different distinguishable detectable moieties. Thus, for example, HEX and FAM fluorescent dyes may be present on different primers in multiplex PCR and associated with the resulting amplicons. In other embodiments, the forward primer is be labeled with one detectable moiety, while the reverse primer is labeled with a different detectable moiety, e.g. FAM dye for a forward primer and HEX dye for a reverse primer. Use of different detectable moieties is useful for discriminating between amplified products which are of the same length or are very similar in length. Thus, in certain embodiments, at least two different fluorescent dyes are used to label different primers used in a single amplification.

Analysis of amplified products from amplification reactions, such as multiplex PCR, can be performed using an automated DNA analyzer such as an automated DNA sequencer (e.g., ABI PRISM 3100 Genetic Analyzer) which can evaluate the amplified products based on size (determined by electrophoretic mobility) and/or respective fluorescent label. Detection of amplification products can also be by melting curve analysis.

In certain embodiments of the aspects provided herein, the methods further comprise a nucleic acid extraction step. Various nucleic acid extraction methods are known in the art which can be employed with the methods and compositions provided herein such as lysis methods (such as alkaline lysis), phenol:chloroform and isopropanol precipitation. Nucleic acid extraction kits can also be used. In suitable embodiments, the extraction method is according to QIAamp™ mini blood kit, Agencourt Genfind™, Roche Cobas®, Roche MagnaPur®, or phenol:chloroform extraction using Eppendorf Phase Lock Gels®.

Oligonucleotides or combinations of oligonucleotides that are useful as primers or probes in the methods are also provided. These oligonucleotides are provided as substantially purified material.

Kits comprising oligonucleotides which may be primers for performing amplifications as described herein also are provided. Kits may further include oligonucleotides that may be used as probes to detect amplified nucleic acid. Kits may also include restriction enzymes for digesting non-target nucleic acid to increase detection of target nucleic acid by the oligonucleotide primers.

DETAILED DESCRIPTION OF THE INVENTION

Figure 1A:
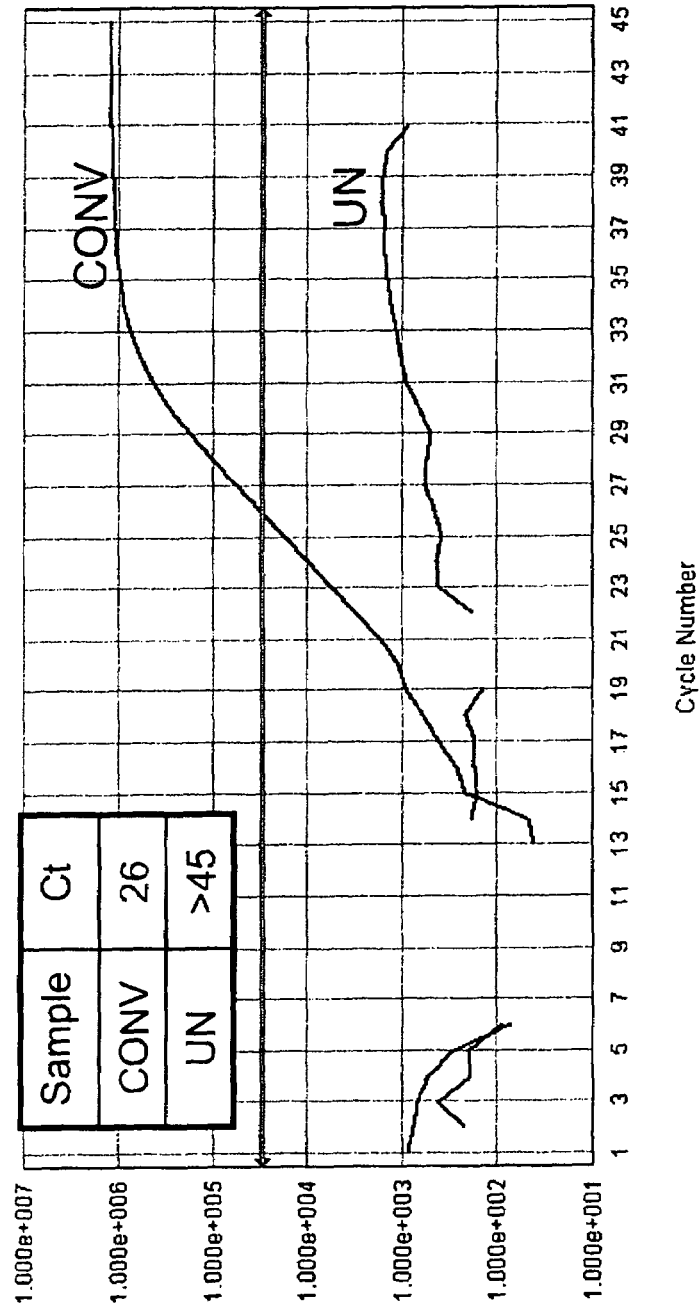
FIGS. 1A and 1B present data showing the amplification of the sequence-modified top strand of integrated SCCmec from converted ("CONV") and unconverted ("UN") DNA derived from a clinical sample. The x-axis shows the number of PCR cycles and the y-axis shows the normalized fluorescence intensity. The threshold cycle (Ct) reflects the cycle number at which the fluorescence generated within a reaction crosses a user-defined threshold (indicated by the horizontal line).

In accordance with the present invention, there are provided methods for identifying methicillin-resistant *S. aureus* (MRSA) and/or methicillin-sensitive *S. aureus* (MSSA) in a biological sample containing nucleic acids by detection of a *S. aureus*-specific gene, the mecA gene, and integrated SCCmec DNA in the same sample.

In one aspect, the present invention provides methods of identifying *S. aureus* (MRSA and/or MSSA) in biological samples that may contain nucleic acids from both *S. aureus* and coagulase-negative Staphylococcal species such as *S. epidermidis* and *S. haemolyticus*. Coagulase-negative Staphylococcal species are less pathogenic than *S. aureus* but share the same habitats and permanently or transiently colonize the anterior nares and regions of skin and mucous membranes that are sources of infection. While not wishing to be limited by theory, a single gene marker may be insufficient to distinguish MRSA from these other less pathogenic strains. For example, mecA is distributed widely among Staphylococcal strains, while the SCCmec cassette carrying mecA is known to integrate into the genomes of *S. aureus, S. epidermidis, S. haemolyticus* and *S. hominis*. Species other than *S. aureus* such as *S. epidermidis* lack additional pathogenic factors, making its identification less clinically significant. Hanssen & Sollid. Antimicrob Agents & Chemother 51:1671 (2007).

Moreover, the integrated SCCmec cassette can undergo genetic rearrangement, which leaves the SCCmec/orfX junction intact, but deletes the mecA gene from the genome. Thus, clinical isolates of methicillin-sensitive *S. aureus* (MSSA) exist that contain remnant portions of the SCCmec cassette lacking an intact mecA gene. These MSSA isolates would be falsely identified as MRSA using identification methods that solely rely upon detection of the SCCmec cassette integrated into the *S. aureus* genome. For this reason, it is desirable that a diagnostic assay detects not only the presence of the SCCmec cassette integrated into the *S. aureus* genome, but also detects the presence of the mecA gene.

Accordingly, the present inventors have surprisingly discovered that a positive identification of MRSA and/or MSSA can be made by detecting three marker nucleic acids in a biological sample. To make a positive identification of MRSA and/or MSSA, the biological sample containing converted nucleic acids is contacted with primer pairs corresponding to a *S. aureus* specific gene (e.g. spa), mecA, and integrated SCCmec. The amplification preferably occurs in a multiplex format, but individual reactions for each marker may also be used. Amplification from all three sequence-modified markers indicates a high likelihood of MRSA in the sample. Amplification from the *S. aureus* specific marker alone, or integrated SCCmec and the *S. aureus* specific gene, but not mecA, indicates that MSSA is likely present in the sample. In accordance with the present invention, methods which distinguish between MRSA and MSSA by detecting mecA, integrated SCCmec, and a *S. aureus* specific marker gene may use converted (i.e. sequence-modified) nucleic acids or may use unconverted nucleic acids for any or all of the three genes.

The present invention is described herein using several definitions, as set forth below and throughout the specification.

As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

As used herein, "about" means plus or minus 10%.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam, et al., Nucleic Acids Res. 2001 Jun. 1; 29(11):E54-E54; Hafner, et al., Biotechniques 2001 April; 30(4):852-860.

The term "complement," "complementary," or "complementarity" as used herein with reference to polynucleotides (i.e., a sequence of nucleotides such as an oligonucleotide or a target nucleic acid) refers to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA. The term "substantially complementary" as used herein means that two sequences specifically hybridize (defined below). The skilled artisan will understand that substantially complementary sequences need not hybridize along their entire length.

As used herein, the term "detecting" used in context of detecting a signal from a detectable label to indicate the presence of a target nucleic acid in the sample does not require the method to provide 100% sensitivity and/or 100% specificity. As is well known, "sensitivity" is the probability that a test is positive, given that the person has a target nucleic acid sequence, while "specificity" is the probability that a test is negative, given that the person does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

A "fragment" in the context of a nucleic acid refers to a sequence of nucleotide residues which are at least about 5 nucleotides, at least about 7 nucleotides, at least about 9 nucleotides, at least about 11 nucleotides, or at least about 17 nucleotides. The fragment is typically less than about 300 nucleotides, less than about 100 nucleotides, less than about 75 nucleotides, less than about 50 nucleotides, or less than 30 nucleotides. In certain embodiments, the fragments can be used in polymerase chain reaction (PCR), various hybridization procedures or microarray procedures to identify or amplify identical or related parts of mRNA or DNA molecules. A fragment or segment may uniquely identify each polynucleotide sequence of the present invention.

"Genomic nucleic acid" or "genomic DNA" refers to some or all of the DNA from a chromosome. Genomic DNA may be intact or fragmented (e.g., digested with restriction endonucleases by methods known in the art). In some embodiments, genomic DNA may include sequence from all or a portion of a single gene or from multiple genes. In contrast, the term "total genomic nucleic acid" is used herein to refer to the full complement of DNA contained in the genome. Methods of purifying DNA and/or RNA from a variety of samples are well-known in the art.

The term "multiplex PCR" as used herein refers to simultaneous amplification of two or more products within the same reaction vessel. Each product is primed using a distinct primer pair. A multiplex reaction may further include specific probes for each product, that are detectably labeled with different detectable moieties.

As used herein, the term "oligonucleotide" refers to a short polymer composed of deoxyribonucleotides, ribonucleotides or any combination thereof. Oligonucleotides are generally between about 10, 11, 12, 13, 14 or 15 to about 150 nucleotides (nt) in length, more preferably about 10, 11, 12, 13, 14, or 15 to about 70 nt, and most preferably between about 18 to about 26 nt in length. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymidine (uracil if RNA); and "M" means adenine or cytosine. An oligonucleotide may be used as a primer or as a probe.

As used herein, a "primer" for amplification is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal expression and amplification. The term "primer" as used herein includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of dsDNA. A "reverse primer" is complementary to the sense-strand of dsDNA.

Primers are typically between about 10 and about 100 nucleotides in length, preferably between about 15 and about 60 nucleotides in length, and most preferably between about 25 and about 40 nucleotides in length. There is no standard length for optimal hybridization or polymerase chain reaction amplification. An optimal length for a particular primer application may be readily determined in the manner described in H. Erlich, PCR Technology, Principles and Application for DNA Amplification, (1989).

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art. As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

As used herein, the term "sample" or "test sample" may comprise clinical samples, isolated nucleic acids, or isolated microorganisms. In preferred embodiments, a sample is obtained from a biological source (i.e., a "biological sample"), such as tissue, bodily fluid, or microorganisms collected from a subject. Sample sources include, but are not limited to, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). Preferred sample sources include nasopharyngeal swabs, wound swabs, and nasal washes. The term "patient sample" as used herein refers to a sample obtained from a human seeking diagnosis and/or treatment of a disease.

As used herein, the term "Scorpion™ detection system" refers to a method for real-time PCR. This method utilizes a bi-functional molecule (referred to herein as a "Scorpion™"), which contains a PCR primer element covalently linked by a polymerase-blocking group to a probe element. Additionally, each Scorpion™ molecule contains a fluorophore that interacts with a quencher to reduce the background fluorescence.

The terms "target nucleic acid" or "target sequence" as used herein refer to a sequence which includes a segment of nucleotides of interest to be amplified and detected. Copies of the target sequence which are generated during the amplification reaction are referred to as amplification products, amplimers, or amplicons. Target nucleic acid may be composed of segments of a chromosome, a complete gene with or without intergenic sequence, segments or portions of a gene with or without intergenic sequence, or sequence of nucleic acids which probes or primers are designed. Target nucleic acids may include a wild-type sequence(s), a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be DNA or RNA extracted from a cell or a nucleic acid copied or amplified therefrom, or may include extracted nucleic acids further converted using a bisulfite reaction.

As used herein "TaqMan® PCR detection system" refers to a method for real time PCR. In this method, a TaqMan® probe which hybridizes to the nucleic acid segment amplified is included in the PCR reaction mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

Sample Preparation

Specimens from which MRSA can be detected and quantified with the present invention are from sterile and/or non-sterile sites. Sterile sites from which specimens can be taken are body fluids such as blood, urine, cerebrospinal fluid, synovial fluid, pleural fluid, pericardial fluid, intraocular fluid, tissue biopsies or endotracheal aspirates. Non-sterile sites from which specimens can be taken are e.g. sputum, stool, swabs from e.g. skin, inguinal, nasal and/or throat. Preferably, specimens are from non-sterile sites, more preferably wound and/or nasal swabs are used in the present invention. Specimens for MRSA detection may also comprise cultures of isolated bacteria grown on appropriate media to form colonies. Specimens may also include bacterial isolates.

Specimens may be processed prior to nucleic acid amplification. In one embodiment, bacteria isolated from clinical specimens may be cultured in media containing antibiotics (e.g. methicillin) to check for the presence of drug resistance. In another embodiment, immunocapture with an antibody specific for S. aureus is used to enrich the sample for this species. To discriminate MRSA from any other methicillin-resistant Staphylococcal species, the assay first detects a species-specific gene product, e.g. spa., using an antibody, and then uses nucleic acid amplification to detect one or more target nucleic acids associated with MRSA (e.g. mecA and/or SCCmec) in the enriched sample. In another embodiment, capture of S. aureus genomic DNA using a specific binding agent, such as a nucleic acid probe or protein nucleic acid, is used to enrich the sample for this species. For example, the assay first detects a species-specific gene product e.g. spa using a nucleic acid probe, and then uses nucleic acid amplification to detect one or more target nucleic acids associated with MRSA (e.g. mecA and/or SCCmec) in the enriched sample. The nucleic acid conversion step may be done before or after the genomic capture step.

The nucleic acid (DNA or RNA) may be isolated from the sample according to any methods well known to those of skill in the art. If necessary the sample may be collected or concentrated by centrifugation and the like. The cells of the sample may be subjected to lysis, such as by treatments with enzymes, heat surfactants, ultrasonication or combination thereof. The lysis treatment is performed in order to obtain a sufficient amount of DNA derived from MRSA and/or MSSA, if present in the sample, to detect using polymerase chain reaction.

Various methods of DNA extraction are suitable for isolating the DNA. Suitable methods include phenol and chloroform extraction. See Maniatis et al., Molecular Cloning, A Laboratory Manual, 2d, Cold Spring Harbor Laboratory Press, page 16.54 (1989). Numerous commercial kits also yield suitable DNA including, but not limited to, QIAamp™ mini blood kit, Agencourt Genfind™, Roche Cobas® Roche MagNA Pure® or phenol:chloroform extraction using Eppendorf Phase Lock Gels®.

Conversion of Nucleic Acids to Modified Nucleic Acids

In one aspect, the nucleic acids present in the sample are converted to sequence-modified nucleic acids prior to amplification. "Conversion" refers to the process whereby the non-methylated cytosines present in the nucleic acids are chemically deaminated and modified into uracils. Following amplification, thymidine residues are substituted for the deaminated cytosines. In some methods, the conversion is accomplished by contacting the nucleic acids with sodium bisulphite. Thus, in unmethylated DNA, this process results in all or mostly all cystosine (C) residues being replaced by thymidine (T), thereby converting a 4 base pair sequence into a 3 base pair sequence of A's, T's and G's. The bisulphite DNA conversion method for the detection of methylated DNA was described in Frommer et al., PNAS 89: 1827-1831 (1992) and Clark et al., Nucl Acids Res 22: 2990-7 (1994). Numerous commercial kits are available to perform the bisulfite conversion reaction including MethylEasy™ (Human Genetic Signatures), EpiTect® Bisulfite Kit (Qiagen/Epigenomics), and MethylAmp™ DNA Modification Kit (Epigentek).

Chemical conversion of cytosine to thymidine residues may be carried out as follows. First, the nucleic acid sample is denatured, if double stranded, to provide single-stranded nucleic acid. The denaturation step may be performed by contacting the nucleic acid with a NaOH solution, or other suitable alkaline reagent, or by heating. Second, the nucleic acid sample is reacted with a reagent and incubated so as to form a treated nucleic acid sample where any methylated nucleotides in the nucleic acid sample remain unchanged while unmethylated cytosine nucleotides are depurinated. Suitable reagents include, but are not limited to, sodium bisulfite. Third, the treated nucleic acid sample is purified to substantially remove any unwanted reagents or diluents from the treated nucleic acid sample. This may be accomplished, for example, by using column purification and concentration, or diluting the sample so as to reduce salt concentration and then precipitating the nucleic acid. Finally, a desulphonation step of the treated nucleic acid sample may be performed to remove sulphonate groups present on the treated nucleic acid so as to obtain a nucleic acid sample substantially free of sulphonate groups. Further detail regarding the conversion of non-methylated nucleotides can be found in U.S. Patent Application publications 2007/0020633, 2004/0219539, and 2004/0086944.

Non-methylated cytosine residues in both DNA strands are converted as a result of the process just described. Consequently, following conversion the two DNA strands are no longer fully complementary and will not specifically hybridize, but may hybridize under non-stringent conditions, depending on the number of non-methylated cytosines within the converted strands. If few non-methylated cytosines are present within the strand, then the strands will likely retain some complementarity after conversion. If many non-methylated cytosines are present within the strand, then the top strand and bottom strand will be less likely to hybridize even under non-stringent conditions. As used herein, the general term "strand" refers to a single chain of sugar-phosphate linked nucleosides, i.e. a strand of double-stranded DNA (dsDNA). The "top strand" refers to the sense strand of the polynucleotide read in the 5' to 3' direction, which is the strand of dsDNA that includes at least a portion of a coding sequence of a functional protein. The "bottom strand" refers to the anti-sense strand, which is the strand of dsDNA that is the reverse complement of the sense strand. It is understood that, while a sequence is referred to as bottom or top strand, such a designation is intended to distinguish complementary strands since, in solution, there is no orientation that fixes a strand as a top or bottom strand. It is also understood that the top strand will therefore have its own complementary strand following amplification and likewise the bottom strand will have its own complementary strand following amplification. While the original converted strands (top or bottom) will be simplified to only contain a 3 base pair sequence of A's, T's and G's, the complementary strands will necessarily only contain T's, A's and C's. In some methods, the presence of converted nucleic acids is detected using PCR. For each target sequence, either the top strand, the bottom strand, or both may be detected using primers specific for the modified sequence of either strand.

Amplification of Nucleic Acids

Nucleic acid samples or isolated nucleic acids may be amplified by various methods known to the skilled artisan. Preferably, PCR is used to amplify nucleic acids of interest. Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase. When the template is sequence-modified, as described above, the amplification mixture preferably does not contain a UNG nuclease.

If the target sequence is present in a sample, the primers will bind to the sequence and the polymerase will cause the primers to be extended along the target sequence by adding on nucleotides. By raising and lowering the temperature of the reaction mixture, the extended primers will dissociate from the marker to form reaction products, excess primers will bind to the marker and to the reaction products and the process is repeated, thereby generating amplification products. Cycling parameters can be varied, depending on the length of the amplification products to be extended. An internal positive amplification control (IPC) can be included in the sample, utilizing oligonucleotide primers and/or probes. The IPC can be used to monitor both the conversion process and any subsequent amplification.

Target Nucleic Acids and Primers

In various embodiments of the present invention, oligonucleotide primers and probes are used in the methods described herein to amplify and detect target sequence-modified nucleic acids specific to MRSA and/or MSSA. In certain embodiments, target nucleic acids may include sequence-modified fragments of the mecA gene, integrated SCCmec, and a marker gene specific to *Staphylococcus aureus* (e.g. spa). In other embodiments, target nucleic acids may include unmodified fragments of the mecA gene, integrated SCCmec, and a marker gene specific to *Staphylococcus aureus* (e.g. spa). In addition, primers can also be used to amplify one or more control nucleic acid sequences. The target nucleic acids described herein may be detected individually or in a multi-plex format, utilizing individual labels for each target.

The skilled artisan is capable of designing and preparing primers that are appropriate for amplifying a target sequence in view of this disclosure. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill in the art.

Specifically, primers and probes to amplify and detect sequence-modified or unmodified nucleic acids corresponding to integrated SCCmec, mecA, and a marker specific to *Staphylococcus aureus* (e.g. spa) are provided by the invention. Primers that amplify a nucleic acid molecule can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis or real-time PCR), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 35 nucleotides in length.

A further consideration for designing primers for sequence-modified nucleic acids is that the converted sequence comprises primarily A, T, and G residues or alternatively primarily T, A and C residues. Accordingly, the melting temperature of the primer directed to a sequence-modified target will typically be lower than a corresponding primer directed to the unmodified target. Therefore, it may be necessary for the length of sequence-modified primers to be adjusted compared to a corresponding unmodified target primer. Therefore, the oligonucleotide primers may be longer than typical oligonucleotide primers directed to sequences comprised of all four bases (e.g., longer than 15 to 35 nucleotides). When the PCR template is sequence modified DNA, the majority of the DNA is effectively reduced to three bases (A, T, and G on one strand and T, A and C on the other strand). This decreases the complexity of DNA and can increase the incidence of primer-template interaction at "non-specific" regions. Optionally, these non-specific interactions may be overcome by the use of a nested or semi-nested PCR approach.

Designing oligonucleotides to be used as hybridization probes can be performed in a manner similar to the design of primers. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 60 nucleotides in length.

In some embodiments, a mix of primers is provided having degeneracy at one or more nucleotide positions. Degenerate primers are used in PCR where variability exists in the target sequence, i.e. the sequence information is ambiguous. Typically, degenerate primers will exhibit variability at no more than about 4, no more than about 3, preferably no more than about 2, and most preferably, no more than about 1 nucleotide position.

The target nucleic acids to identify MRSA may be selected according to a wide variety of methods. Exemplary target nucleic acids are modified sequences corresponding to mecA integrated SCCmec, and a marker specific to *Staphylococcus aureus* (e.g. spa). The target may be amplified in full. Alternatively, in some embodiments, fragments or segments of the target sequences are amplified. The fragment may be derived from any region of the full sequence, but fragment length in accordance with the present methods is typically at least 30, at least 50, at least 75, at least 100, at least 150, at least 200, at least 250 or at least 300 nucleotides. As will be understood by one of skill in the art, the size and location of the particular target nucleic acid will control the selection of the amplification primers and vice versa.

In some embodiments, specific primers and probes are selected to amplify and detect a modified fragment of a marker gene specific for *S. aureus*. This marker should be present in *S. aureus*, but absent from other *Staphylococcus* species. Examples of specific marker genes include, but are not limited to spa, agr, ssp protease, sir, sodM, cap, coa, alpha hemolysin, gamma hemolysin, femA, Tuf, sortase, fibrinogen binding protein, clfB, srC, sdrD, sdrE, sdrF, sdrG, sdrH, NAD synthetase, sar, sbi, rpoB, gyrase A, and orfX. The detection of a *S. aureus*-specific gene helps to distinguish a sample containing *S. aureus* from one that may contain other less pathogenic species or strains, e.g., *S. epidermidis*. Thus, amplification of a sequence-modified *S. aureus*-specific gene, together with sequence-modified mecA and sequence-modified integrated SCCmec distinguishes between MRSA and methicillin-resistant *S. epidermidis* (MRSE) and MSSA. One suitable marker gene is the 1.55 kb spa gene (see, for example, GenBank Accession No. NC_002952, range 125378-123828). Exemplary primer/Scorpion™ sequences for amplifying and detecting sequence-modified spa include: SEQ ID NOS 10 and 35 and 11 and 25 and 39 and 26. The skilled artisan will understand that other primers, probes, and Scorpions™ may be used.

In some embodiments, specific primers and probes are selected to amplify and detect a fragment of the 2.0 kb mecA gene (see, for example, GenBank Accession No. AB033763) or a fragment of the sequence-modified mecA gene. Exemplary primer/Scorpion™ sequences for amplifying and detecting sequence-modified mecA include: SEQ ID NOS 12 and 36 and 13, and 27 and 40 and 28. The skilled artisan will understand that other primers, probes, and Scorpions™ may be used.

In some embodiments, specific primers and probes are selected to amplify and detect a fragment of the integrated SCCmec or sequence-modified integrated SCCmec cassette. To detect this sequence, primers are designed so that the amplified fragment contains the junction between the SCCmec cassette and the surrounding genomic DNA. The primers may be designed to amplify either the 5' or 3' junction of sequence-modified SCCmec integrated within the *S. aureus* genome. Preferably the 3' junction of sequence-modified SCCmec is amplified. In particular, a forward primer may be designed to specifically hybridize to the 3' end of sequence-modified SCCmec and a reverse primer designed to specifically hybridize to the sequence-modified or fX gene in the chromosomal DNA surrounding the sequence-modified SCCmec. Exemplary primer/Scorpion™ sequences for amplifying and detecting sequence-modified integrated SCCmec include: SEQ ID NOS 1 and 33, 2 and 34, and 3-9, and 14 and 37, and 15 and 38, and 16-24. The skilled artisan will understand that other primers, probes, and Scorpions™ may be used.

In a suitable embodiment, PCR is performed using a Scorpion™ primer/probe combination. Scorpion™ probes, as used in the present invention comprise a 3' primer with a 5' extended probe tail comprising a hairpin structure which possesses a fluorophore/quencher pair. During PCR, the polymerase is blocked from extending into the probe tail by the inclusion of hexethlyene glycol (HEG). During the first round of amplification the 3' target-specific primer anneals to the target and is extended such that the Scorpion™ is now incorporated into the newly synthesized strand, which possesses a newly synthesized target region for the 5' probe. During the next round of denaturation and annealing, the probe region of the Scorpion™ hairpin loop will hybridize to the target, thus separating the fluorophore and quencher and creating a measurable signal. Such probes are described in Whitcombe et al., Nature Biotech 17: 804-807 (1999).

Detection of a Amplified Nucleic Acids

Amplification of nucleic acids can be detected by any of a number of methods well-known in the art such as gel electrophoresis, column chromatography, hybridization with a probe, sequencing, melting curve analysis, or "real-time" detection.

In one approach, sequences from two or more fragments of interest are amplified in the same reaction vessel (i.e. "multiplex PCR"). Detection can take place by measuring the end-point of the reaction or in "real time." For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the TaqMan® system, Scorpion™ primer system and use of intercalating dyes for double stranded nucleic acid.

In end-point detection, the amplicon(s) could be detected by first size-separating the amplicons, then detecting the size-separated amplicons. The separation of amplicons of different sizes can be accomplished by, for example, gel electrophoresis, column chromatography, or capillary electrophoresis. These and other separation methods are well-known in the art. In one example, amplicons of about 10 to about 150 base pairs whose sizes differ by 10 or more base pairs can be separated, for example, on a 4% to 5% agarose gel (a 2% to 3% agarose gel for about 150 to about 300 base pair amplicons), or a 6% to 10% polyacrylamide gel. The separated nucleic acids can then be stained with a dye such as ethidium bromide and the size of the resulting stained band or bands can be compared to a standard DNA ladder.

In another example, Invader™ (Third Wave Technologies, Inc.) may be used to detect specific nucleic acid sequences after linear or exponential amplification. In the Invader™ assay, the DNA structure recognized by a thermostable flap endonuclease (FEN), is formed by an Invader™ probe that overlaps the signal probe by at least one base. The unpaired single-stranded flap of the signal probe is released during the FEN reaction and can be detected by various methods such as measuring fluorescence after capturing and extending the released signal probe flap with fluorescein-labeled nucleotides (ELISA-format), mass-spectrometry, denaturing gel electrophoresis, etc. A variation of the Invader™ assay uses a FRET probe. The released signal probe fragment of the initial FEN reaction subsequently serves as an Invader probe invading the stem fragment of the hairpin formed intramolecularly in the FRET probe. This process induces a second FEN reaction during which the fluorophore in the FRET probe is separated from the nearby quenching dye in the FRET probe, resulting in the generation of fluorescence. Both FEN reactions occur at isothermic conditions (near the melting temperature of the probes) which enables a linear signal amplification.

In another embodiment, two or more fragments of interest are amplified in separate reaction vessels. If the amplification is specific, that is, one primer pair amplifies for one fragment of interest but not the other, detection of amplification is sufficient to distinguish between the two types—size separation would not be required.

In some embodiments, amplified nucleic acids are detected by hybridization with a specific probe. Probe oligonucleotides, complementary to a portion of the amplified target sequence may be used to detect amplified fragments. Hybridization may be detected in real time or in non-real time. Amplified nucleic acids for each of the target sequences may be detected simultaneously (i.e., in the same reaction vessel) or individually (i.e., in separate reaction vessels). In preferred embodiments, the amplified DNA is detected simultaneously, using two or more distinguishably-labeled, gene-specific oligonucleotide probes, one which hybridizes to the first target sequence and one which hybridizes to the second target sequence. For sequence-modified nucleic acids, the target may be independently selected from the top strand or the bottom strand. Thus, all targets to be detected may comprise top strand, bottom strand, or a combination of top strand and bottom strand targets.

The probe may be detectably labeled by methods known in the art. Useful labels include, e.g., fluorescent dyes (e.g., Cy5®, Cy3®, FITC, rhodamine, lanthamide phosphors, Texas red, FAM, JOE, Cal Fluor Red 610®, Quasar 670®), $^{32}$P, $^{35}$S, $^{3}$H, $^{14}$C, $^{125}$I, $^{131}$I, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

One general method for real time PCR uses fluorescent probes such as the TaqMan® probes, molecular beacons, and Scorpions. Real-time PCR quantitates the initial amount of the template with more specificity, sensitivity and reproducibility, than other forms of quantitative PCR, which detect the amount of final amplified product. Real-time PCR does not detect the size of the amplicon. The probes employed in Scorpion™ and TaqMan® technologies are based on the principle of fluorescence quenching and involve a donor fluorophore and a quenching moiety.

In a preferred embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion™ type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on R-6, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from decreased distance between the donor and the quencher (acceptor fluorophore).

Suitable fluorescent moieties include the following fluorophores known in the art: 4-acetamido-4'-isothiocyanatostilbene-2,2'disulfonic acid, acridine and derivatives (acridine, acridine isothiocyanate) Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Black Hole Quencher™ (BHQ™) dyes (biosearch Technologies), BODIPY® R-6G, BOPIPY®R 530/550, BODIPY® FL, Brilliant Yellow, coumarin and derivatives (coumarin, 7-amino-4-methylcoumarin (AMC, Coumarin 120), 7-amino-4-trifluoromethylcoumarin (Coumarin 151)), Cy2®, Cy3®, Cy3.5®, Cy5®, Cy5.5®, cyanosine, 4',6-diaminidino-2-phenylindole (DAPI), 5',5''-dibromopyrogallol-sulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse™ (Epoch Biosciences Inc.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET)), fluorescamine, IR144, IR1446, Malachite Green isothiocyanate, 4-methylumbelliferone, ortho cresolphthalein, nitrotyrosine, pararosaniline, Phenol Red, B-phycoerythrin, R-phycoerythrin, o-phthaldialdehyde, Oregon Green®, propidium iodide, pyrene and derivatives (pyrene, pyrene butyrate, succinimidyl 1-pyrene butyrate), QSY® 7, QSY® 9, QSY® 21, QSY® 35 (Molecular Probes), Reactive Red 4 (Cibacron® Brilliant Red 3B-A), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red)), N,N,N',N'-tetramethyl-6-carboxyrhodamine (TAMRA), tetramethyl rhodamine, tetramethyl rhodamine isothiocyanate (TRITC), riboflavin, rosolic acid, terbium chelate derivatives.

Other fluorescent nucleotide analogs can be used, see, e.g., Jameson, 278 Meth. Enzymol. 363-390 (1997); Zhu, 22 Nucl. Acids Res. 3418-3422 (1994). U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

The detectable label can be incorporated into, associated with or conjugated to a nucleic acid. Label can be attached by spacer arms of various lengths to reduce potential steric hindrance or impact on other useful or desired properties. See, e.g., Mansfield, 9 Mol. Cell. Probes 145-156 (1995). Detectable labels can be incorporated into nucleic acids by covalent or non-covalent means, e.g., by transcription, such as by random-primer labeling using Klenow polymerase, or nick translation, or amplification, or equivalent as is known in the art. For example, a nucleotide base is conjugated to a detectable moiety, such as a fluorescent dye, and then incorporated into nucleic acids during nucleic acid synthesis or amplification.

With Scorpion™ probes, sequence-specific priming and PCR product detection is achieved using a single molecule. The Scorpion™ probe maintains a stem-loop configuration in the unhybridized state. The fluorophore is attached to the 5' end and is quenched by a moiety coupled to the 3' end, although in suitable embodiments, this arrangement may be switched The 3' portion of the stem also contains sequence that is complementary to the extension product of the primer. This sequence is linked to the 5' end of a specific primer via a non-amplifiable monomer. After extension of the Scorpion™ primer, the specific probe sequence is able to bind to its complement within the extended amplicon thus opening up the hairpin loop. This prevents the fluorescence from being quenched and a signal is observed. A specific target is amplified by the reverse primer and the primer portion of the Scorpion™, resulting in an extension product. A fluorescent signal is generated due to the separation of the fluorophore from the quencher resulting from the binding of the probe element of the Scorpion™ to the extension product.

TaqMan® probes (Heid, et al., Genome Res 6: 986-994, 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi, et al., 16 Nature Biotechnology 49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

In a suitable embodiment, real time PCR is performed using any suitable instrument capable of detecting fluorescence from one or more fluorescent labels. For example, real time detection on the instrument (e.g. a ABI Prisms 7900HT sequence detector) monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually.

In some embodiments, melting curve analysis may be used to detect an amplification product. Melting curve analysis involves determining the melting temperature of an nucleic acid amplicon by exposing the amplicon to a temperature gradient and observing a detectable signal from a fluorophore. Melting curve analysis is based on the fact that a nucleic acid sequence melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides.

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. In some embodiments, the fluorescent dye for determining the melting temperature of a nucleic acid may be excited by different wavelength energy than any other of the different fluorescent dyes that are used to label the oligonucleotides. In some embodiments, the second fluorescent dye for determining the melting temperature of the detected nucleic acid is an intercalating agent. Suitable intercalating agents may include, but are not limited to SYBR™ Green 1 dye, SYBR dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixture thereof. In suitable embodiments, the selected intercalating agent is SYBR™ Green 1 dye.

By detecting the temperature at which the fluorescence signal is lost, the melting temperature can be determined. In the disclosed methods, each of the amplified target nucleic acids may have different melting temperatures. For example, each of these amplified target nucleic acids may have a melting temperature that differs by at least about 1° C., more preferably by at least about 2° C., or even more preferably by at least about 4° C. from the melting temperature of any of the other amplified target nucleic acids. The melting temperature(s) of the MRSA targets from the respective amplification product can confirm the presence or absence of MRSA and/or MSSA in the sample.

To minimize the potential for cross contamination, reagent and mastermix preparation, specimen processing and PCR setup, and amplification and detection are all carried out in physically separated areas.

The following examples serve to illustrate the present invention. These examples are in no way intended to limit the scope of the invention.

Example 1

Conversion of Native Nucleic Acids to Sequence Modified Nucleic Acids

Genomic DNA was extracted from 6 nasal swab specimens using the QIAamp™ mini blood kit (Qiagen) extraction procedure with the ATL buffer modification. Nasal swab specimens were stored at −20° C. prior to extraction. Just prior to extraction, the swabs were thawed at room temperature for 20 minutes, 500 μL 1×PBS was added to the swab and the vial containing the swab followed by gentle agitation to mix. 450 μL of the suspension was then transferred to a 1.5 ml microcentrifuge tube and the suspension was centrifuged at 14,000 rpm for 10 min. The supernatant was carefully aspirated and the pellet was resuspended in 180 μL of Buffer ATL from the QIAamp™ mini blood kit. This kit was used to extract DNA according to the manufacturer's instructions. Eluted genomic DNA was split into two samples: one for conversion of nucleic acids to sequence modified nucleic acids ("converted DNA") and the other was not converted ("unconverted DNA").

Genomic DNA was converted using the MethylEasy™ Fast kit (Human Genetic Signatures). The manufacturer's protocol was followed. At the end of the procedure, converted DNA was eluted in 2 steps, each using 15 μL reagent 5 from the MethylEasy™ Fast kit for a total elution volume of 30 μL.

Example 2

Amplification of Sequence Modified Nucleic Acids

Top Strand Assays

To detect the sequence-modified top strand of integrated SCCmec, seven forward primers and two Scorpion™ oligonucleotides containing a reverse orfx primer and probe were designed. These primers detect the top strand of sequence modified integrated SCCmec MREJ (mec right extreme junction), types i & ii, iii, iv, v, and vii (Table 1). The forward primers were each specific to a single SCCmec type, but the Scorpion™ primer/probe, which hybridizes to orfx was not specific for any single SCCmec type. One Scorpion™ primer/probe and five forward primers are combined to detect sequence-modified SCCmec cassette types ii, iii, iv, v, and vii.

To determine the specificity of the primers shown in Table 1 for sequence-modified top strand of integrated SCCmec, samples of "converted DNA" or "unconverted DNA" were analyzed in singleplex reactions. A 10× Primer Mix was prepared using 0.1×TE pH 8 as the diluent. Final concentrations of each component in the 10× mix indicated in parenthesis: SA4-MTopF1.1 (2 μM), SA4-MTop2.1 (2 μM), SA4-MTop3.1, (2 μM) SA4-MTopF4 (2 μM), SA4-MTop5 (2 μM), SA4-MSRTop1 (2 μM) or SA4-MSRTop2 (2 μM). The reaction mix for a single well of a 96-well optical PCR plate included the following: 12.5 μL 2× Master Mix; 2.5 μL of 10× Primer Mix (components listed above); 4.0 μL Nuclease-free water; 1.0 μL Internal control amplicon; 5.0 μL "converted DNA" or "unconverted DNA" template (250 pg). The conditions for the real time PCR run on a Applied Biosystems AB7500 were as follows: Step 1: 95° C. 10 min; Step 2: 95° C. 15 sec; Step 3: 60° C. 35 sec. Steps 2-3 were repeated for a total of 45 cycles. Sequence-modified integrated SCCmec was detected with Cal Fluor Red 610.

TABLE 1

Top Strand Assay Scorpions and Primers for Integrated SCCmec

| SCCmec MREJ Type | Top Strand Scorpion ™ or Primer Name (SEQ ID NO) | Sequence |
| --- | --- | --- |
| Scorpion ™ (types i, ii, iii, iv, v, vii) | SA4-MSRTop1 (SEQ ID NOS 1 and 33) | 5' quencher-AGGCGG TTGTAAGATGTTTTTGTG TAGGTTGTCCGCCTdye/ blocker-AAAACAAAAC |

TABLE 1-continued

Top Strand Assay Scorpions and Primers for Integrated SCCmec

| SCCmec MREJ Type | Top Strand Scorpion ™ or Primer Name (SEQ ID NO) | Sequence |
|---|---|---|
| | | AACTTTATWTTCATCATT AACA3' |
| Scorpion ™ (types i, ii, iii, iv, v, vii) | SA4-MSRTop2 (SEQ ID NOS 2 and 34) | 5' quencher-AGGCGG AATGTTATTTTGTTRAAT GATAGTGtCCGCCT- dye/blocker-AACAAC CTACACAAAAACATCTTA CAACA 3' |
| i, ii | SA4-MTopF1.1 (SEQ ID NO: 3) | 5' TATTTGAAATGAAAG ATTGTGGAGGTTA 3 |
| iii | SA4-MTopF2.1 (SEQ ID NO: 4) | 5' TATGATATTGTAAGG TATAATTTAATATTTTAT ATATGTA 3' |
| iii | SA4-MTopF2.2 (SEQ ID NO: 5) | 5' TATTATTAATTTTTT AATTTAATTGTAGTTTTA TAATTAA 3' |
| iv | SA4-MTopF3.1 (SEQ ID NO: 6) | 5' GTATGATATTGTAAG GTATAATTTAATATTTTA TATATGT 3' |
| iv | SA4-MTopF3.2 (SEQ ID NO: 7) | 5' AATATTGTATGATAT TGTAAGGTATAATTTAAT ATTTTA 3' |
| v | SA4-MTopF4 (SEQ ID NO: 8) | 5' ATAAAATTATGGTTG AAATAATTGTATTATTTA TGA 3' |
| vii | SA4-MTopF5 (SEQ ID NO: 9) | 5' AAACAAGTTGATTTA TATATTATGTATTAAATA ATGGAA 3' |

Figure 1B:
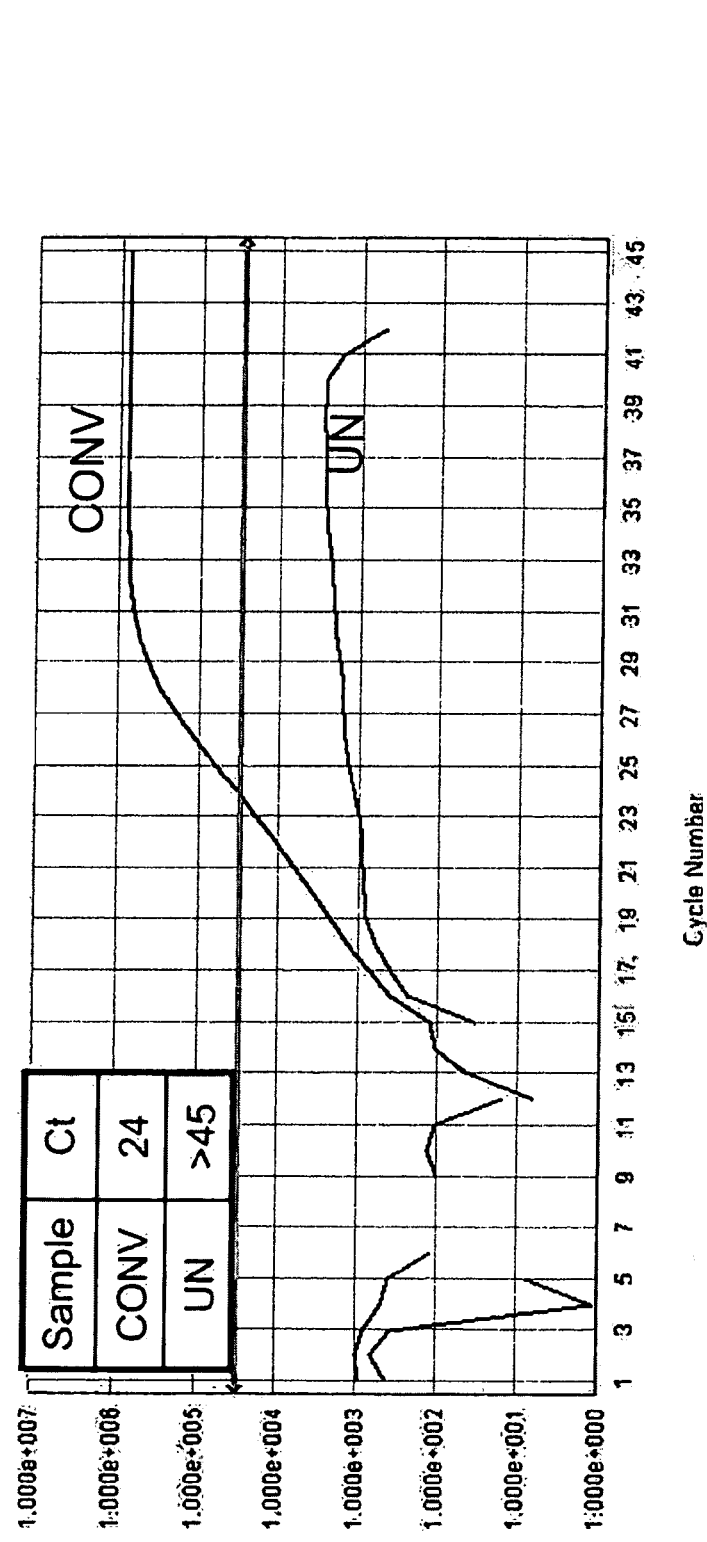

The results of detecting the sequence-modified top strand of integrated SCCmec are shown in FIG. 1A (using SA4-MSRTop1 Scorpion™) and FIG. 1B (using SA4-MSRTop2 Scorpion™). The data indicate that the primers and probes are specific for sequence-modified integrated SCCmec, and do not detect unconverted integrated SCCmec within 45 cycles.

Figure 2:
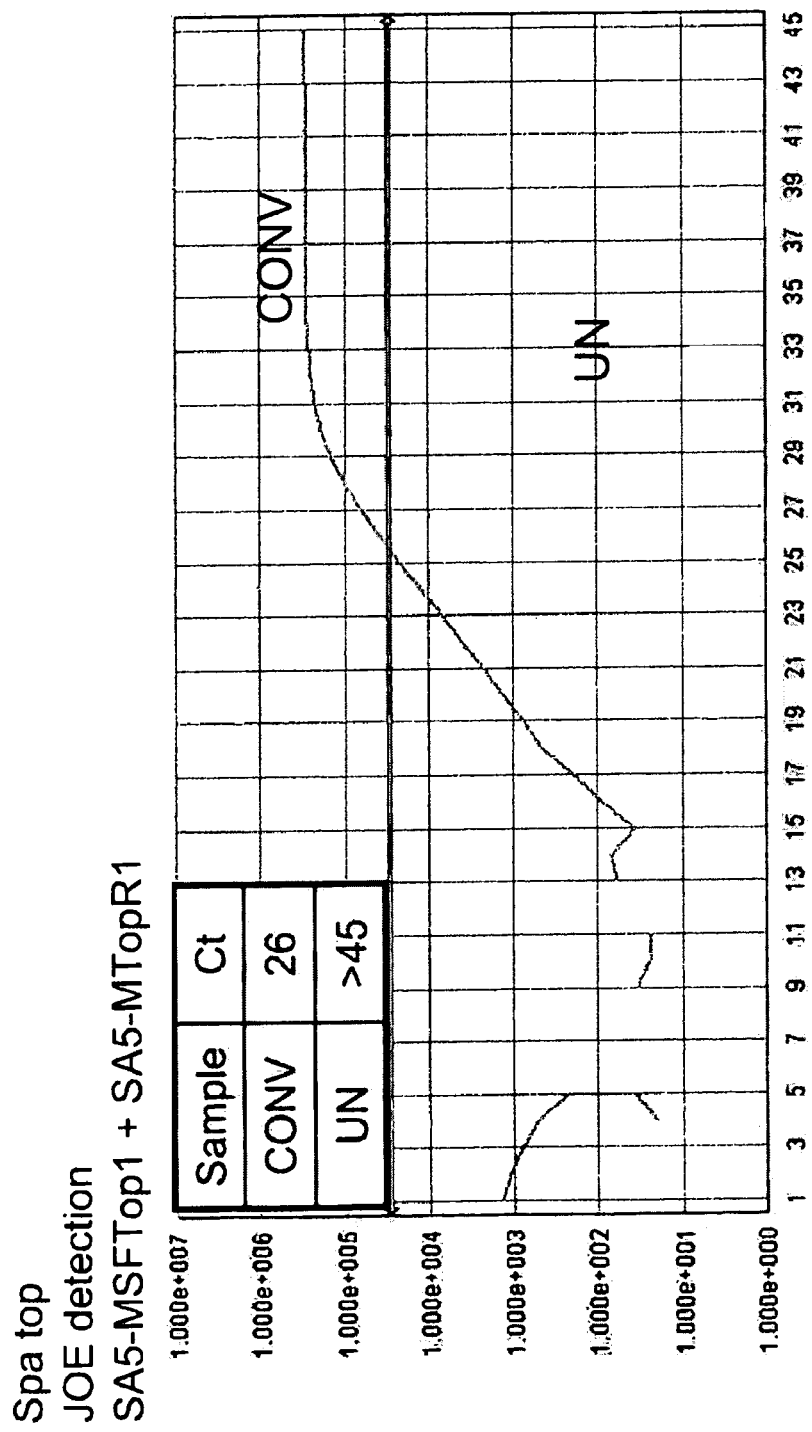
FIG. 2 presents data showing the amplification of the sequence-modified top strand of the spa marker from converted ("CONV") and unconverted ("UN") DNA derived from a clinical sample.

One Scorpion™ oligonucleotide (containing a forward primer and a probe) and a reverse primer were designed to detect the sequence-modified top strand of the spa gene (Table 2). To determine the specificity of the primers shown in Table 2 for the sequence-modified top strand of spa gene from S. aureus, samples of "converted DNA" or "unconverted DNA" were analyzed in singleplex reactions. Using the same PCR conditions described above, except with primers/probe SA5-MSFTop1 (2 µM) (JOE detection) and SA5-MTopR1 (2 µM), the results indicate that the primers and probes are specific for sequence-modified spa, and do not detect unconverted spa within 45 cycles (FIG. 2).

TABLE 2

Top Strand Assay Scorpions and Primers for spa

| Top Strand Scorpion ™ or Primer Name (SEQ ID NO) | Sequence |
|---|---|
| SA5-MSFTop1 (SEQ ID NOS 10 and 35) | 5' quencher-ACCCCCAACAAATAT TACACCACCAAATATAACCCCCT- dye/blocker-TTACCTCTACCTATT CTATTTCTAATTTTACCTATA 3' |
| SA5-MTopR1 (SEQ ID NO: 11) | 5' CTTAAATCATCTTTAAAACTTTAA ATAAAACCA 3' |

Figure 3:
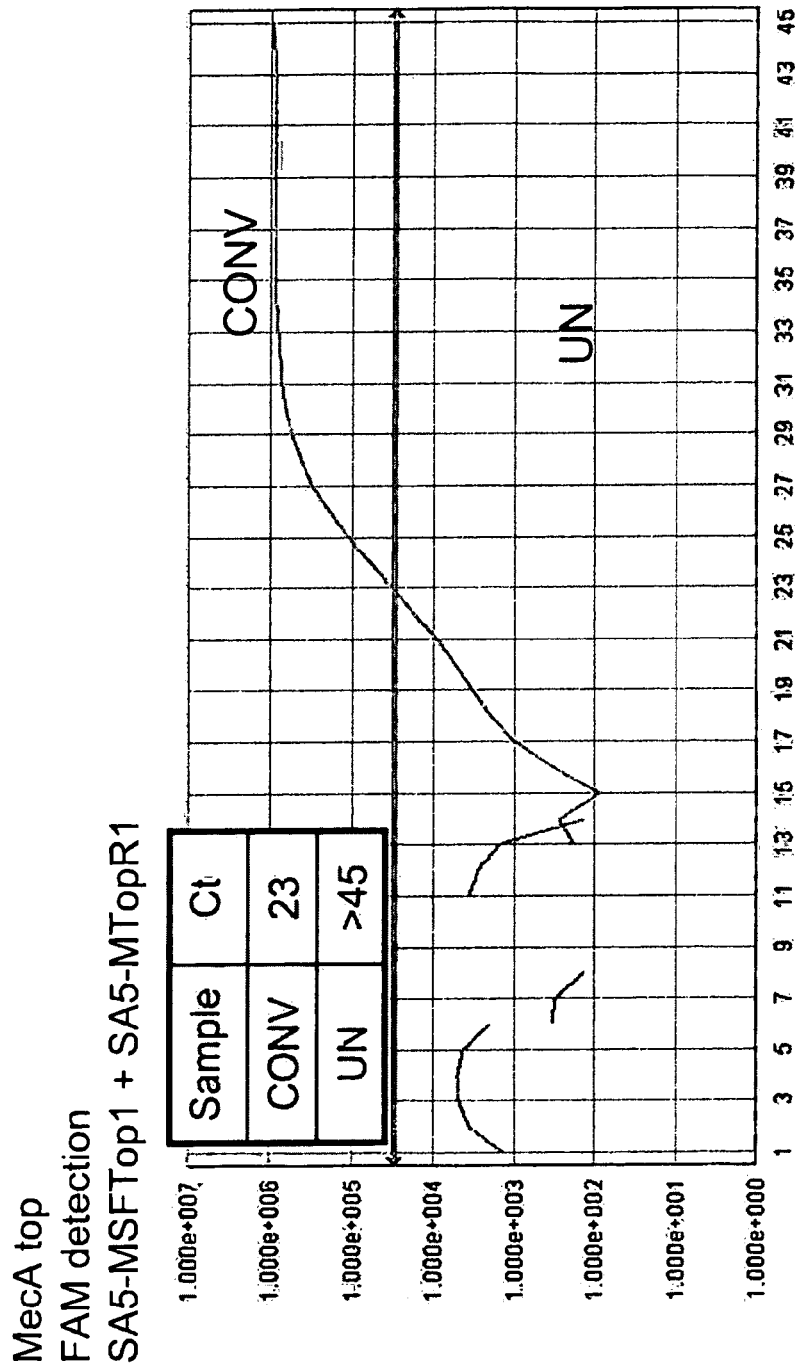
FIG. 3 presents data showing the amplification of the sequence-modified top strand of the mecA marker from converted ("CONV") and unconverted ("UN") DNA derived from a clinical sample.

One Scorpion™ oligonucleotide (containing a forward primer and a probe) and a reverse primer were designed to detect the sequence-modified top strand from the mecA gene (Table 3). To determine the specificity of the primers shown in Table 3 for the sequence-modified top strand of mecA gene, samples of "converted DNA" or "unconverted DNA" were analyzed in singleplex reactions. Using the same PCR conditions described above, except with primers/probe SA1-MS-FTop1 (2 µM) (FAM detection) and SA1-MTopR1 (2 µM), the results indicate that the primers and probes are specific for sequence-modified mecA, and do not detect unconverted mecA within 45 cycles (FIG. 3).

TABLE 3

Top Strand Assay Scorpions and Primers for mecA

| Top Strand Scorpion ™ or Primer Name (SEQ ID NO) | Sequence |
|---|---|
| SA1-MSFTop1 (SEQ ID NOS 12 and 36) | 5' quencher-AGCGCCATTATTTT CTAATACACTATAAATTAAAAAAATC TGGCGCT-dye/blocker-TTTAGG TTATGGATAAGGTGAAATATTGATT A 3' |
| SA1-MTopR1: (SEQ ID NO: 13) | 5' TCTTTATATATTTTATTTACAAC TTATTACATACCATCA 3' |

Bottom Strand Assay

To detect the sequence-modified bottom strand of integrated SCCmec, seven forward primers and two Scorpion™ primer/probes containing a reverse orfx primer and probe were designed. The forward primers were designed to detect the bottom strand of sequence modified integrated SCCmec types ii, iii, iv, v, and vii (Table 4). The forward primers were each specific to a single SCCmec type, but the Scorpion™ primer/probe, which hybridizes to orfx was not specific for a SCCmec type. To determine the specificity of the primers shown in Table 4 for sequence-modified bottom strand of integrated SCCmec, samples of "converted DNA" or "unconverted DNA" were analyzed in singleplex reactions using the PCR conditions described above, except that primers included: SA4-MFBot1 (2 µM), SA4-MFBot2 (2 µM), SA4-MFBot3 (2 µM), SA4-MFBot4 (2 µM), SA4-MFBot5.1 (2 µM (SA4-MSRBot1 or SA4-MSRBot2 (2 µM) (Cal Fluor Red 610 detection).

TABLE 4

Bottom Strand Assay Scorpions and Primers for Integrated SCCmec

| SCCmec MREJ Type | Bottom Strand Scorpion™ or Primer Name (SEQ ID NO) | Sequence |
|---|---|---|
| Scorpion™ (types i. ii, iii, iv. v, vii) | SA4-MSRBot1 (SEQ ID NOS 14 and 37) | 5' quencher-AGCGCCA TTTAATCCACCAATAACAA ATACGGCGCT-dye/ blocker-GAATTGAATTA ATGTATGATTTAAGGGTAA AGTGA 3' |
| Scorpion™ (types ii, iii, iv, v, vii) | SA4-MSRBot2 (SEQ ID NOS 15 and 38) | 5' quencher-AGCCGGC TACATTATAAAACATCCTT ATACAAACCGGCT dye/ blocker-GTGATTTTGTA TTTGTTATTGGTGGAT TA 3' |
| i & ii | SA4-MFBot1 (SEQ ID NO: 16) | 5' TTACTTAAAATAAAAA ACTACAAAAACTAACTATA TCAAA 3' |
| iii | SA4-MFBot2 (SEQ ID NO: 17) | 5' CTCTATAAACATCATAT AATATTACAAAATATAATC CA 3' |
| iv | SA4-MFBot3 (SEQ ID NO: 18) | 5' TAAAAACCACTACTAAA AAAAATATAAAAATCC A 3' |
| v | SA4-MFBot4 (SEQ ID NO: 19) | 5' AACTCTACTTTATATT ATAAAATTACAACTAAAAT AACCA 3' |
| v | SA4-MBotF4.1 (SEQ ID NO: 20) | 5' ACAACTAAAATAACCA CATCATTTATAATATACTT CT 3' |
| vii | SA4-MFBot5.1 (SEQ ID NO: 21) | 5' ACTTACTACAAACATC TAATACAAAAAAAAATC AA 3' |
| vii | SA4-MFBot5.2 (SEQ ID NO: 22) | 5' AAAAAAATCAATTTAC ACACCATATATTAAATAAT AA 3' |
| vii | SA4-MBot5.3 (SEQ ID NO: 23) | 5' CTCATATTTTTTAATT TTATTTATAATACACTT CT 3' |
| vii | SA4-MBot5.4 (SEQ ID NO: 24) | 5' TTTTCTCATATTTTTT AATTTTATTTATAATACAC TTCT3' |

Figure 4A:
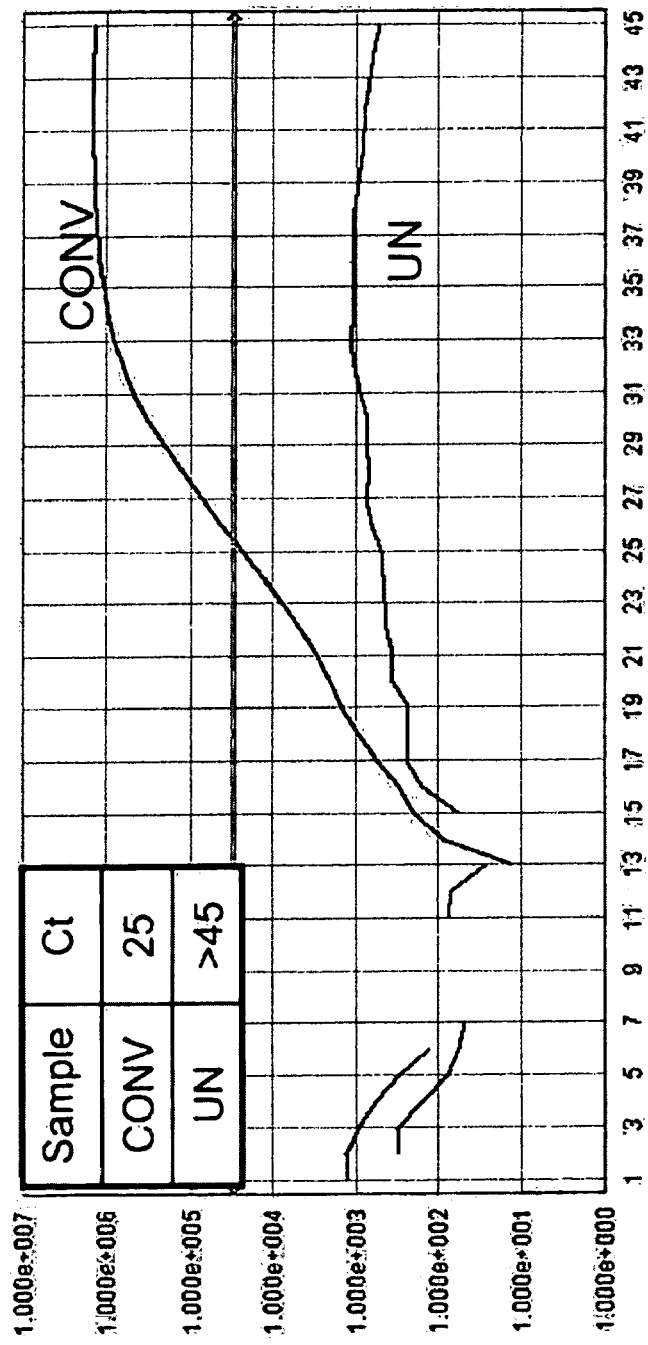
FIGS. 4A and 4B present data showing the amplification of the sequence-modified bottom strand of integrated SCCmec from converted ("CONV") and unconverted ("UN") DNA derived from a clinical sample.
Figure 4B:
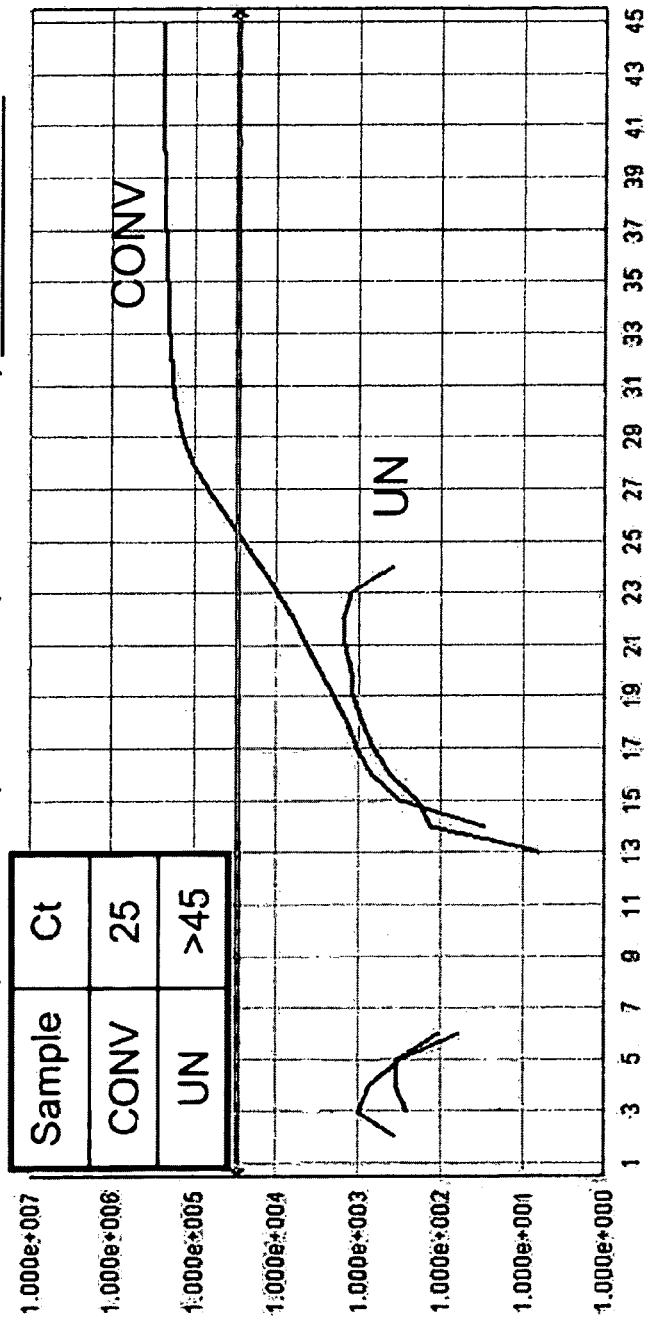

The results of detecting the sequence-modified bottom strand of integrated SCCmec are shown in FIG. 4A (using SA4-MSRBot1 Scorpion™) and FIG. 4B (SA4-MSRBot2 Scorpion™). The data indicate that the primers and probes are specific for sequence-modified integrated SCCmec, and do not detect unconverted integrated SCCmec within 45 cycles.

Figure 5:
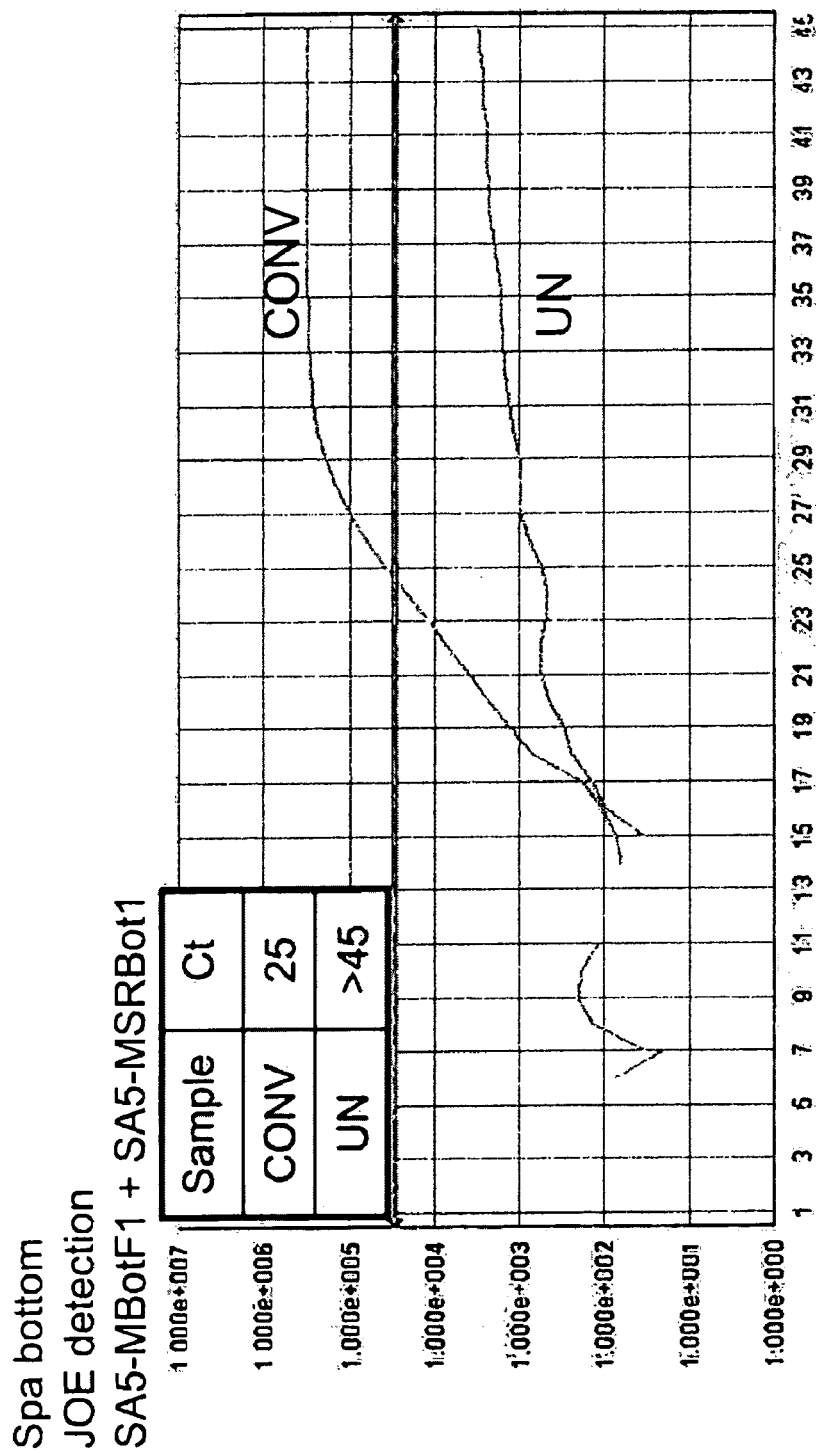
FIG. 5 presents data showing the amplification of the sequence-modified bottom strand of the spa marker from converted ("CONV") and unconverted ("UN") DNA derived from a clinical sample.

One Scorpion™ oligonucleotide (containing a forward primer and a probe) and a reverse primer were designed to detect the sequence-modified bottom strand of the spa gene from *S. aureus* (Table 5). To determine the specificity of the primers shown in Table 5 for the sequence-modified bottom strand of spa gene from *S. aureus*, samples of "converted DNA" or "unconverted DNA" were analyzed in singleplex reactions. Using the same PCR conditions described above, except with primers/probe SA5-MSRBot1 (2 µM) (JOE detection) and SA5-MBotF1 (2 µM), the results indicate that the primers and probes are specific for sequence-modified spa, and do not detect unconverted spa within 45 cycles (FIG. 5).

TABLE 5

Bottom Strand Assay Scorpions and Primers for spa

| Bottom Strand Scorpion™ or Primer Name (SEQ ID NO) | Sequence |
|---|---|
| SA5-MSRBot1 (SEQ ID NOS 25 and 39) | 5' quencher-AGCGGCAAATATTAAATATACCT AACTTAAACACTAATCGCCGCTdye/blocker-T TTGGATTATTTTTAAGGTTTTGGATAAAATTA 3' |
| SA5-MBotF1 (SEQ ID NO: 26) | 5' ATCTAATAACATAACACCTACTACAATACTAC ACAA 3' |

Figure 6:
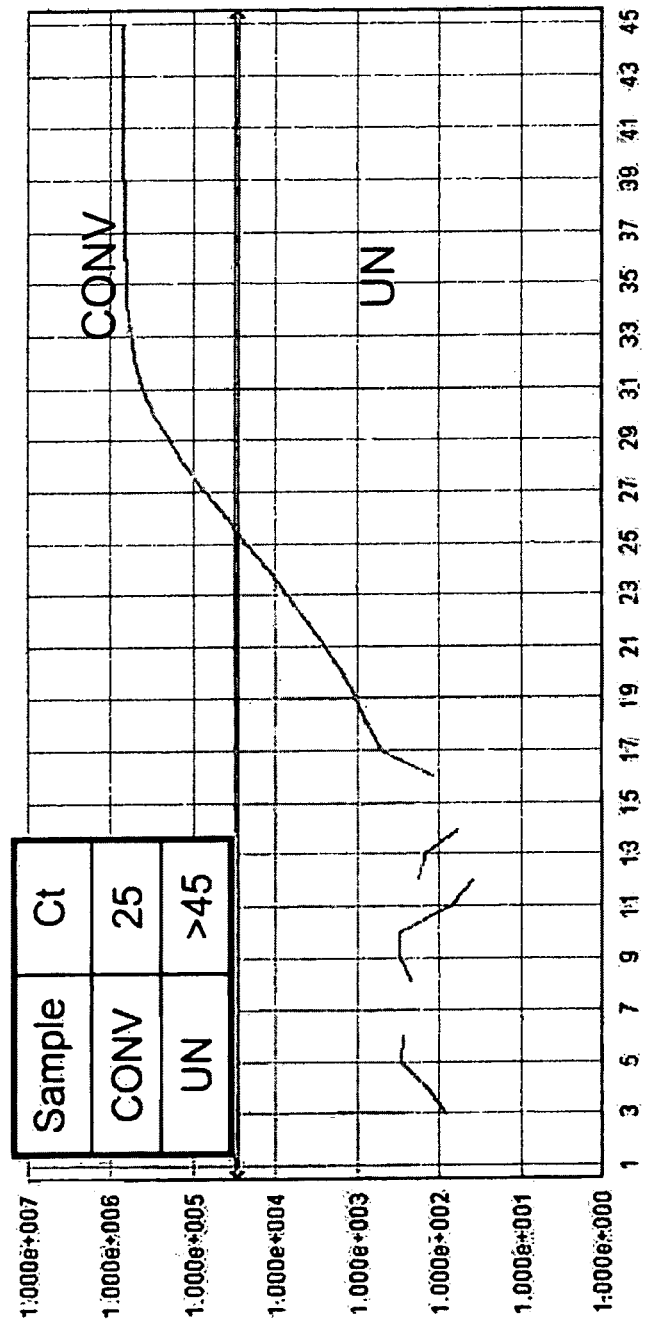
FIG. 6 presents data showing the amplification of the sequence-modified bottom strand of the mecA marker from converted ("CONV") and unconverted ("UN") DNA derived from a clinical sample.

One Scorpion™ oligonucleotide (containing a forward primer and a probe) and a reverse primer were designed to detect the sequence-modified bottom strand from the mecA gene (Table 6). To determine the specificity of the primers shown in Table 6 for the sequence-modified top strand of mecA gene, samples of "converted DNA" or "unconverted DNA" were analyzed in singleplex reactions. Using the same PCR conditions described above, except with primers/probe SA1-MSFBot1 (2 µM) (FAM detection) and SA1-MBotR1 (2 µM), the results indicate that the primers and probes are specific for sequence-modified mecA, and do not detect unconverted mecA within 45 cycles (FIG. 6)

TABLE 6

Bottom Strand Assay Scorpions and Primers for mecA

| Bottom Strand Scorpion™ or Primer Name (SEQ ID NO) | Sequence |
|---|---|
| SA1-MSFBot1 (SEQ ID NOS 27 and 40) | 5' quencher-AGCGCCGTGTTTATAGATTGAAA GGATTTGTATTGGCGCT-dye/blocker-ACTGA TTCAAATTACAAACAAAATAAAATACTAA 3' |
| SA1-MBotR1 (SEQ ID NO: 28) | 5' GTTTTTTAATAAGTGAGGTGTGTTAATATTGT TA 3' |

Example 3

Multiplex Amplification and Detection of Sequence-Modified Nucleic Acids

A multiplex assay for sequence-modified spa, mecA, integrated SCCmec, and an internal control, was performed using the following Scorpion™ oligonucleotides and primers. A 10× Primer Mix was prepared using 0.1×TE pH 8 as the diluent. Final concentrations of each component in the 10× mix indicated in parenthesis: SA5-MSFTop1 (2 µM); SA5-MTopR1 (2 µM); SA1-MSFTop1 (2 µM); SA1-MTopR1 (2 µM); SA4-MSRTop2 (2 µM); SA4-MTopF1.1 (2 µM); SA4-MTop2.1 (2 µM); SA4-MTop3.1 (2 µM); SA4-MTopF4 (2 µM); SA4-MTopF5 (2 µM); IC-noloop-SFP-Dx2-DQ (1 µM); IC-SR4-Dx2 (1 µM). The reaction mix for a single well of a 96-well optical PCR plate included the following: 12.5

μL 2× Master Mix; 2.5 μL of 10× Primer Mix (components listed above); 4.0 μL Nuclease-free water; 1.0 μL Internal control amplicon; 5.0 μL bisulfite converted genomic DNA template (250 pg). The conditions for the real time PCR run on a Applied Biosystems AB7500 were as follows: Step 1: 95° C. 10 min; Step 2: 95° C. 15 sec; Step 3: 60° C. 35 sec. Steps 2-3 were repeated for a total of 45 cycles. Spa is detected with JOE, integrated SCCmec is detected with Cal Fluor Red 610, mecA is detected with FAM, and the internal positive control was detected with Quasar 670.

Figure 7:
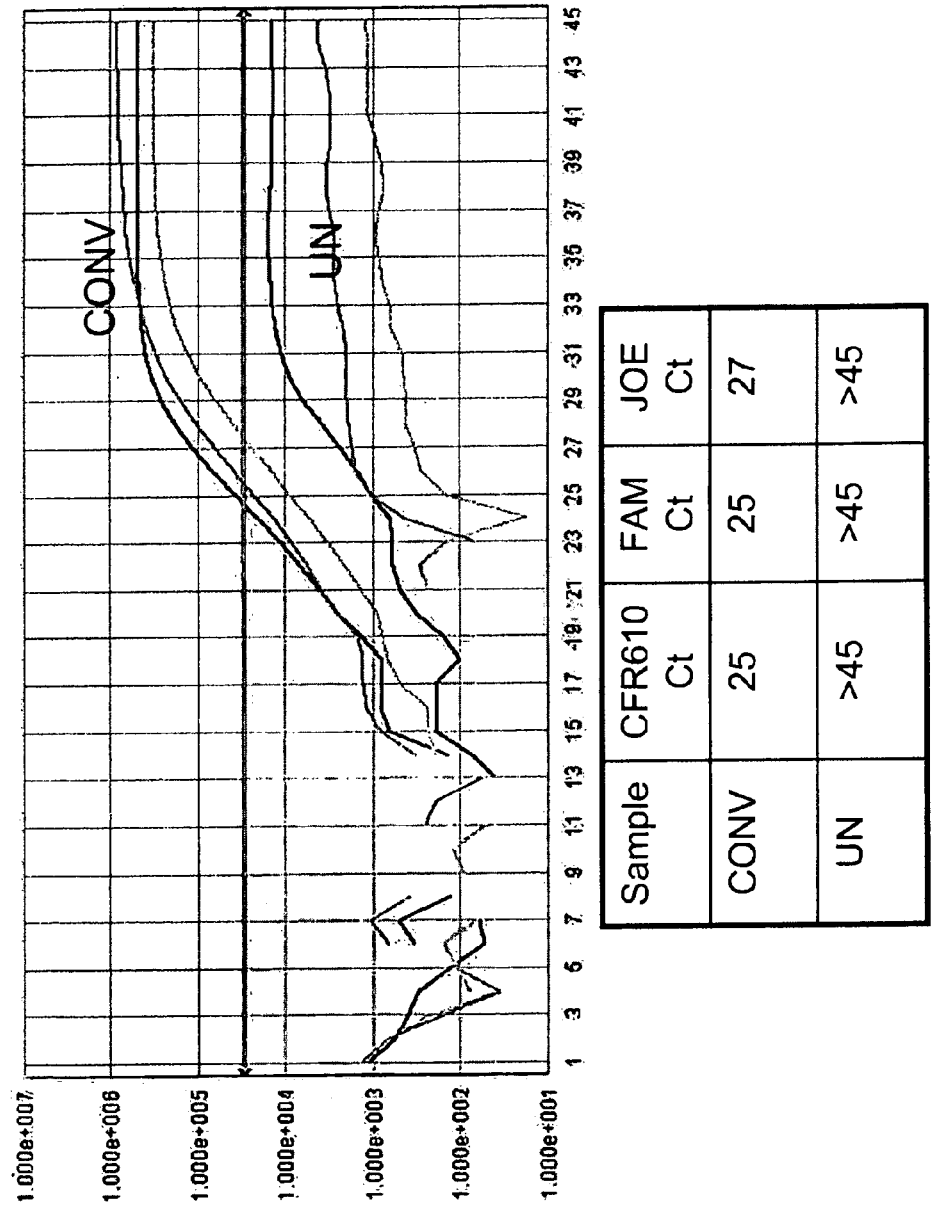
FIG. 7 presents data showing the multiplex amplification the sequence-modified integrated SCCmec, spa, and mecA from converted ("CONV") and unconverted ("UN") DNA derived from a clinical sample.

The results are shown in FIG. 7 and indicate that the assay can simultaneously positively identify sequence-modified nucleic acids corresponding to target genes from sequence-modified MRSA contained within a clinical specimen, but not detect target genes from unmodified MRSA. The data shown here was produced by using a nasal swab clinical specimen known to be positive for MRSA. The nucleic acids in the specimen were extracted using the QIAamp kit. Half of the genomic extraction was saved as "unmodified nucleic acids" and the other half was converted with HQS MethylEasy Fast™. Both sequence modified (converted) sample and unmodified sample were then used as template for a multiplex reaction using the primers and probes described above.

Example 4

Detection of Unmodified spa and mecA

Figure 8:
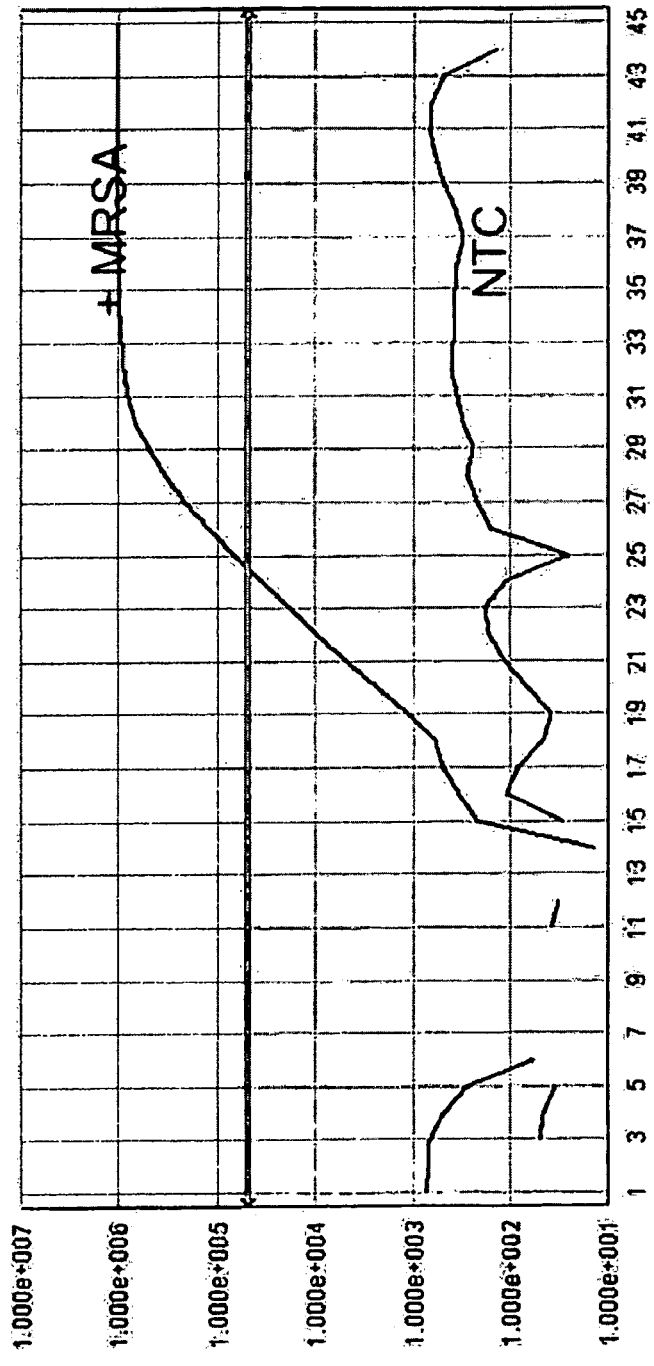
FIG. 8 presents data showing the amplification of the spa marker from a clinical sample.

One Scorpion™ oligonucleotide (containing a forward primer and a probe) and a reverse primer were designed to detect the spa gene (Table 7). Using the same PCR conditions described above, except with primers/probe SA5-SF2A-DQS (2 μM) (Cal Fluor Red 610 detection) and SA5-R2C (2 μM). The results indicate that the primers and probes are capable of detecting spa in a MRSA sample (FIG. 8).

TABLE 7

Scorpions and Primers for Unmodified spa

| Top Strand Scorpion ™ or Primer Name (SEQ ID NO) | Sequence |
| --- | --- |
| SA5-SF2A-DQS (SEQ ID NOS 29 and 41) | 5' quencher-AGGCCACCAGATATAAGTAATGT ACCTAAAGTGGCCT-dye/blocker-ATTCGTAA ACTAGGTGTAGGTATTGCA 3' |
| SA5-R2C (SEQ ID NO: 30) | 5' ACTTGATAAAAAGCATTTTGTTGAGCT 3' |

Figure 9:
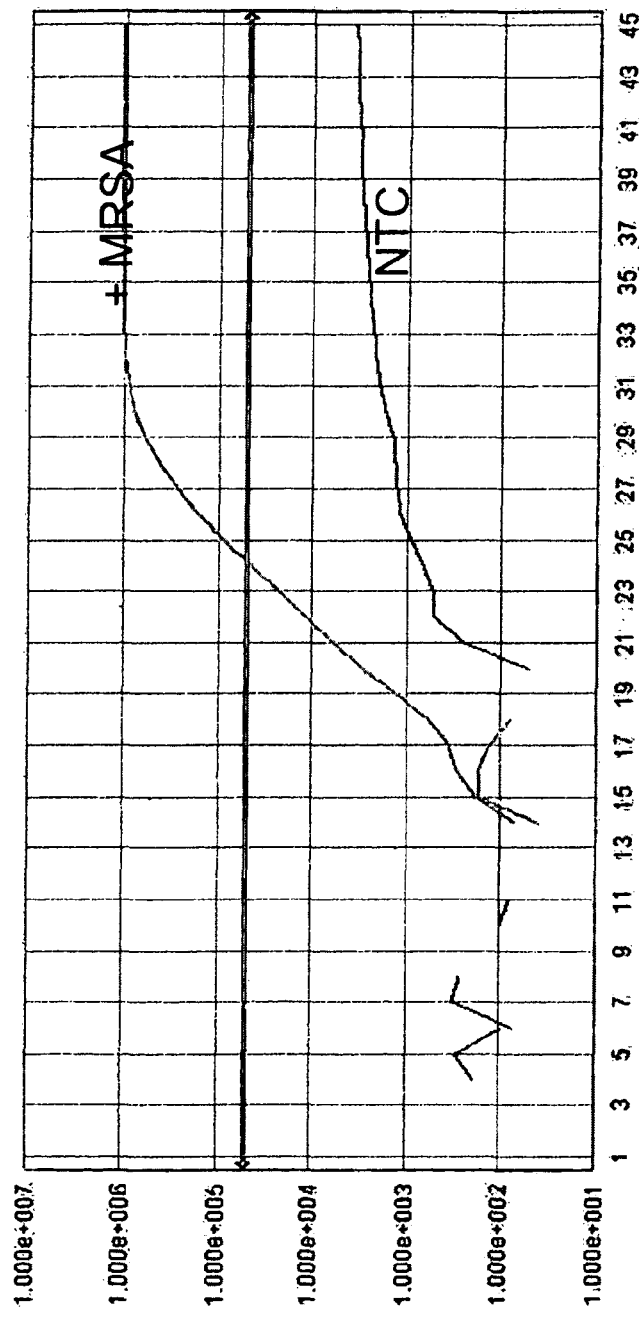
FIG. 9 presents data showing the amplification of the mecA marker from a clinical sample.

One Scorpion™ oligonucleotide (containing a forward primer and a probe) and a reverse primer were designed to detect the mecA gene (Table 8). Using the same PCR conditions described above, except with primers/probe SA1-SF11C-DQS (2 μM) (FAM detection) and SA1-R11.2 (2 μM). The results indicate that the primers and probes are capable of detecting mecA in a MRSA sample (FIG. 9).

TABLE 8

Scorpions and Primers for Unmodified mecA

| Top Strand Scorpion™ or Primer Name (SEQ ID NO) | Sequence |
| --- | --- |
| SA1-SF11C-DQS (SEQ ID NOS 31 and 42)) | 5' quencher-AGCCGCTATAGATTGAAAGGATC TGTACTGGCGGCT-dye/blocker-AGGTTACGG ACAAGGTGAAATACTGA 3' |
| SA1R11.2 (SEQ ID NO: 32) | 5' GTGAGGTGCGTTAATATTGCCATTA 3' |

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

SEQUENCE LISTING

The instant application contains a Sequence Listing which has been submitted via EFS-Web and is hereby incorporated by reference in its entirety. Said. ASCII copy, created on May 17, 2010, is named 54769942.txt and is 9,872 bytes in size.

Other embodiments are set forth within the following claims.

What is claimed is:

1. A method for detecting *Staphylococcus aureus* in a biological sample comprising:
   (a) converting the non-methylated cytosines present in the nucleic acids contained in a biological sample, to uracils to produce sequence-modified nucleic acids,
   (b) bringing the biological sample containing the sequence modified nucleic acids in contact with:
      (i) a first primer pair which is complementary to a segment of a marker gene specific for *Staphylococcus aureus* of the sequence modified nucleic acids;
      (ii) a second primer pair which is complementary to a segment of the mecA gene of the sequence modified nucleic acids; and
      (iii) a third primer pair, one primer of which is complementary to a segment of SCCmec of the sequence modified nucleic acids and the other primer of which is complementary to a segment of the orfx gene of the sequence modified nucleic acids;
      under conditions wherein the primers specifically hybridize and amplification products of the sequence-modified nucleic acids are produced; and
   (c) identifying the modified nucleic acids from *Staphylococcus aureus* by detecting the amplification product produced by one or more of the primer pairs.

2. The method of claim 1, wherein the biological sample is contacted with the first primer pair, the second primer pair, and the third primer pair in a multiplex amplification reaction.

3. The method of claim 1, wherein the marker gene specific for *Staphyloccocus aureus* is selected from the group consisting of: spa, agr, ssp protease, sir, sodM, cap, coa, alpha hemolysin, gamma hemolysin, femA, Tuf, sortase, fibrinogen binding protein, clfB, srC, sdrD, sdrE, sdrF, sdrG, sdrH, NAD synthetase, sar, sbi, rpoB, gyrase A, and orfX.

4. The method of claim 3, wherein the marker gene specific for *Staphylococcus aureus* is spa.

5. The method according to claim 1, wherein the converting step is accomplished by contacting the nucleic acids with sodium bisulfite.

6. The method according to claim 1, wherein one or more of the primers is degenerate.

7. The method according to claim 1, wherein said detecting is accomplished using a labeled oligonucleotide probe for each amplification product.

8. The method according to claim 7, wherein the amplification is performed using real time PCR.

9. The method according to claim 8, wherein, for each amplification product to be detected, the probe and one of the primers of the primer pair are part of the same primer/probe molecule.

10. The method according to claim 1, wherein one or both of the primers of the first primer pair comprises a sequence selected from the group consisting of SEQ ID NOS 10 and 35 and 11.

11. The method according to claim 1, wherein one or both of the primers of the second primer pair comprises a sequence selected from the group consisting of SEQ ID NOS 12 and 36 and 13.

12. The method according to claim 1, wherein one or both of the primers of the third primer pair comprises a sequence selected from the group consisting of SEQ ID NOS 1 and 33, 2 and 34, and 3-9.

13. The method according to claim 1, wherein one or both of the primers of the first primer pair comprises a sequence selected from the group consisting of SEQ ID NOS 25 and 39 and 26.

14. The method according to claim 1, wherein one or both of the primers of the second primer pair comprises a sequence selected from the group consisting of SEQ ID NOS 27 and 40 and 28.

15. The method according to claim 1, wherein one or both of the primers of the third primer pair comprises a sequence selected from the group consisting of SEQ ID NOS 14 and 37, 15 and 38, and 16-24.

16. A method for determining if a biological sample from an individual contains methicillin resistant *Staphylococcus aureus* (MRSA) or methicillin sensitive *Staphylococcus aureus* (MSSA), comprising:
   (a) converting the non-methylated cytosines present in the nucleic acids contained in the biological sample, to uracils to produce sequence-modified nucleic acids,
   (b) bringing the biological sample containing the sequence modified nucleic acids in contact with:
      (i) a first primer pair which is complementary to a segment of a marker gene specific for *Staphylococcus aureus* of the sequence modified nucleic acids;
      (ii) a second primer pair which is complementary to a segment of the mecA gene of the sequence modified nucleic acids; and
      (iii) a third primer pair, one primer of which is complementary to a segment of SCCmec of the sequence modified nucleic acids and the other primer of which is complementary to a segment of the orfx gene of the sequence modified nucleic acids;
      under conditions wherein the primers specifically hybridize and amplification products of the sequence-modified nucleic acids are produced; and
   (c) identifying the modified nucleic acids from *Staphylococcus aureus* by detecting the amplification product produced by one or more of the primer pairs, wherein
      (i) amplification of all three sequence-modified nucleic acids indicates MRSA in the sample; and
      (ii) amplification of the *S. aureus* specific marker gene alone, or a segment of SCCmec and the *S. aureus* specific marker gene, but not mecA, indicates MSSA in the sample.

17. The method of claim 16, wherein the marker gene specific for *Staphyloccocus aureus* is selected from the group consisting of: spa, agr, ssp protease, sir, sodM, cap, coa, alpha hemolysin, gamma hemolysin, femA, Tuf, sortase, fibrinogen binding protein, clfB, srC, sdrD, sdrE, sdrF, sdrG, sdrH, NAD synthetase, sar, sbi, rpoB, gyrase A, and orfX.

18. The method according to claim 16, wherein the converting step is accomplished by contacting the nucleic acids with sodium bisulfite.

19. The method according to claim 16, wherein one or more of the primers is degenerate.

20. The method according to claim 16, wherein said detecting is accomplished using a labeled oligonucleotide probe for each amplification product.

21. The method according to claim 20, wherein, for each amplification product to be detected, the probe and one of the primers of the primer pair are part of the same molecule.

22. The method according to claim 16, wherein one or both of the primers of the first primer pair comprises a sequence selected from the group consisting of SEQ ID NOS 10 and 35 and 11.

23. The method according to claim 16, wherein one or both of the primers of the second primer pair comprises a sequence selected from the group consisting of SEQ ID NOS 12 and 36 and 13.

24. The method according to claim 16, wherein one or both of the primers of the third primer pair comprises a sequence selected from the group consisting of SEQ ID NOS 1 and 33, 2 and 34, and 3-9.

25. The method according to claim 16, wherein one or both of the primers of the first primer pair comprises a sequence selected from the group consisting of SEQ ID NOS 25 and 39 and 26.

26. The method according to claim 16, wherein one or both of the primers of the second primer pair comprises a sequence selected from the group consisting of SEQ ID NOS 27 and 40 and 28.

27. The method according to claim 16, wherein one or both of the primers of the third primer pair comprises a sequence selected from the group consisting of SEQ ID NOS 14 and 37, 15 and 38, and 16-24.

28. A method of identifying a methicillin-resistant *Staphylococcus aureus* (MRSA) or methicillin sensitive *Staphylococcus aureus* (MSSA), if present, in a biological sample, comprising:
(a) converting the non-methylated cytosines present in the nucleic acids contained in a biological sample, to uracils to produce sequence-modified nucleic acids,
(b) bringing the biological sample in contact with:
(i) a first primer pair which is complementary to a marker gene specific for *Staphylococcus aureus*;
(ii) a second primer pair which is complementary to the mecA gene; and
(iii) a third primer pair, one primer of which is complementary to SCCmec and the other primer of which is complementary to the orfx gene; under conditions wherein the primers specifically hybridize and amplify the marker gene, mecA gene, SCCmec and orfx gene, and
(c) identifying the MSSA and/or MRSA by detecting an amplification product produced by all of the three primer pairs, wherein
(i) amplification of all three sequence-modified nucleic acids indicates MRSA in the sample; and
(ii) amplification of the *S. aureus* specific marker gene alone, or a segment of SCCmec and the *S. aureus* specific marker gene, but not mecA, indicates MSSA in the sample.

29. The method of claim 28, wherein the marker gene specific for *Staphyloccocus aureus* is selected from the group consisting of: spa, agr, ssp protease, sir, sodM, cap, coa, alpha hemolysin, gamma hemolysin, femA, Tuf, sortase, fibrinogen binding protein, clfB, srC, sdrD, sdrE, sdrF, sdrG, sdrH, NAD synthetase, sar, sbi, rpoB, gyrase A, and orfX.

* * * * *

UNITED STATES PATENT AND TRADEMARK OFFICE
CERTIFICATE OF CORRECTION

| | | |
|---|---|---|
| PATENT NO. | : 7,888,075 B2 | Page 1 of 1 |
| APPLICATION NO. | : 12/177075 | |
| DATED | : February 15, 2011 | |
| INVENTOR(S) | : Larry McCarthy et al. | |

It is certified that error appears in the above-identified patent and that said Letters Patent is hereby corrected as shown below:

Column 1, line 29, delete the word "furuneulosis" and replace with --furunculosis--.

Column 5, FIG. 7, lines 35 and 36, delete the phrase "amplification the" and replace with --amplification of the--.

Column 18, line 18, delete the phrase "switched The" and replace with --switched. The--.

Signed and Sealed this

Thirteenth Day of September, 2011

David J. Kappos
*Director of the United States Patent and Trademark Office*